(12) United States Patent
Szokol et al.

(10) Patent No.: US 12,018,005 B1
(45) Date of Patent: Jun. 25, 2024

(54) BLARCAMESINE CO-CRYSTALS FOR THE MANUFACTURE OF PHARMACEUTICAL DOSAGE FORM

(71) Applicant: EGIS GYÓGYSZERGYÁR ZRT., Budapest (HU)

(72) Inventors: Zsuzsanna Szokol, Budapest (HU); Tamás Nagy, Budapest (HU); András Balázs Dancsó, Budapest (HU); Attila Virág, Budapest (HU); Regina Némethné Csillag, Budapest (HU); Károly Lozsi, Budapest (HU); Balázs Volk, Budapest (HU); László Szlávik, Budapest (HU)

(73) Assignee: EGIS GYÓGYSZERGYÁR ZRT., Budapest (HU)

( * ) Notice: Subject to any disclaimer, the term of this patent is extended or adjusted under 35 U.S.C. 154(b) by 0 days.

(21) Appl. No.: 18/225,925

(22) Filed: Jul. 25, 2023

(51) Int. Cl.
 *C07D 307/14* (2006.01)
(52) U.S. Cl.
 CPC ........ *C07D 307/14* (2013.01); *C07B 2200/13* (2013.01)
(58) Field of Classification Search
 None
 See application file for complete search history.

(56) References Cited

FOREIGN PATENT DOCUMENTS

WO  WO 2017/013498  * 1/2017 ........... C07D 307/14
WO  WO 2023/208133  * 11/2023 ........... C07D 307/14

* cited by examiner

*Primary Examiner* — Craig D Ricci
(74) *Attorney, Agent, or Firm* — MILLEN, WHITE, ZELANO & BRANIGAN, P.C.; Csaba Henter

(57) ABSTRACT

$ZnCl_2$ co-crystal of racemic-(±)-blarcamesine hydrochloride of formula 2a, $ZnCl_2$ co-crystal of (S)-(−)-blarcamesine hydrochloride of formula 2b and $ZnCl_2$ co-crystal of (R)-(+)-blarcamesine hydrochloride of formula 2c, processes for preparation thereof and pharmaceutical preparation thereof and methods of treating neurodegenerative, neurodevelopmental diseases such as Alzheimer's disease, Parkinson's disease dementia and/or Rett syndrome.

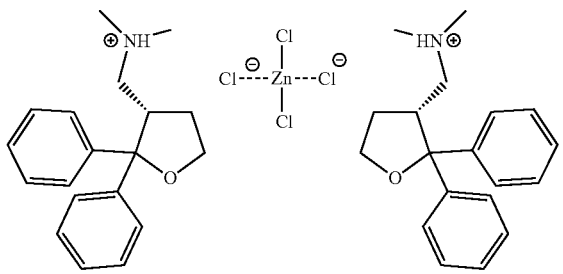

2a

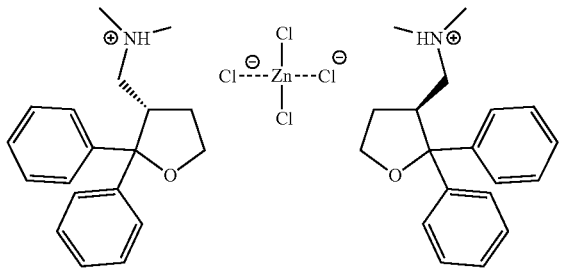

2b

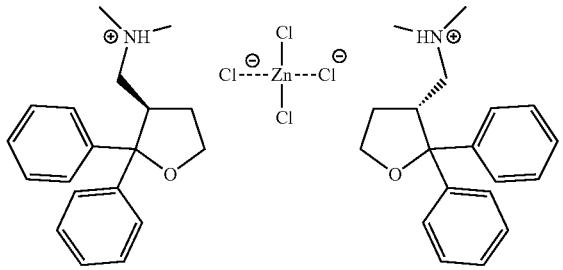

2c

10 Claims, 14 Drawing Sheets

BLARCAMESINE CO-CRYSTALS FOR THE MANUFACTURE OF PHARMACEUTICAL DOSAGE FORM

BACKGROUND OF THE INVENTION

Blarcamesine hydrochloride (ANAVEX2-73) is an investigational drug of Anavex Life Sciences that acts as a 61 receptor agonist and muscarinic receptor modulator. It is in Phase II-III human clinical trials and is being developed for the treatment of Alzheimer's disease and neuroprotective and neurodevelopmental disorders. It is also being developed for the treatment of Parkinson's disease-associated dementia (PDD) and rare paediatric diseases with orphan status (Rett syndrome and infantile spasms).

Blarcamesine molecule has a single asymmetric carbon unit.

The synthesis of racemic blarcamesine base is described in International Publications WO 9730983 and WO 2013008044.

Several methods for the preparation of enantiomers of the blarcamesine base are described in International Publication WO 2013008044 and hydrochloric acid salt is also disclosed.

Three polymorphic forms of blarcamesine hydrochloride are disclosed in International Publication WO 2017013498 as well as a polymorphic form of a metabolite of blarcamesine base (ANAVEX19-144) prepared by two different methods. The metabolite is characterized in detail like blarcamesine HCl API.

International Publication WO 2019200345 of Anavex discloses the crystalline forms of blarcamesine in freebase and salt forms (hydrochloric acid salt and several other salts).

Teva Pharmaceuticals discloses some further salts in its International Publication WO 2021158586.

SUMMARY OF THE INVENTION

The characteristics of solid forms of active pharmaceutical ingredient influence the key properties of the formulations they are used in, such as dissolution affecting bioavailability, stability and determine the range of applicable pharmaceutical technology procedures.

Therefore, the preparation of solid forms of active pharmaceutical ingredients (polymorphs, co-crystals, salts, solvates, complexes) and the study of their properties is an important and essential part of the drug development process.

The object of our invention was to develop a new, pharmaceutically acceptable form of the active ingredient blarcamesine hydrochloride that would retain its uniformity during pharmaceutical processing (crushing, granulation, tableting), in stability studies required for drug development, and in use.

A further object was to develop a simple and economical process for the production of this form on an industrial scale.

First aspect of our invention is the co-crystal of formula 2a consisting of $ZnCl_2$ and racemic-(±)-[(S)-(−), (R)-(+) (1:1)] blarcamesine hydrochloride, as IUPAC name of [(2, 2-diphenyloxolan-3-yl)methyl]dimethylamine hydrochloride, of formula 1a; the co-crystal of formula 2b consisting of $ZnCl_2$ and (S)-(−)-blarcamesine hydrochloride of formula 1b and the co-crystal of formula 2c consisting of $ZnCl_2$ and (R)-(+)-blarcamesine hydrochloride of formula 1c.

In the molecular formulas the dotted bonds relate to the coordinative bonds between the active pharmaceutical ingredient (blarcamesine hydrochloride) and co-crystal former ($ZnCl_2$; ="coformer"), in the same crystal lattice.

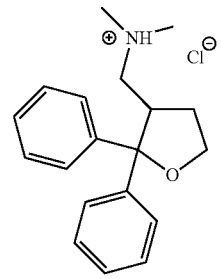

1a

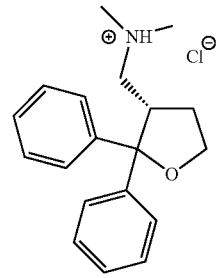

1b

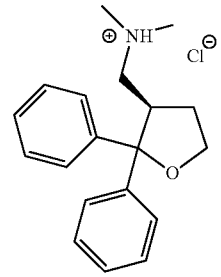

1c

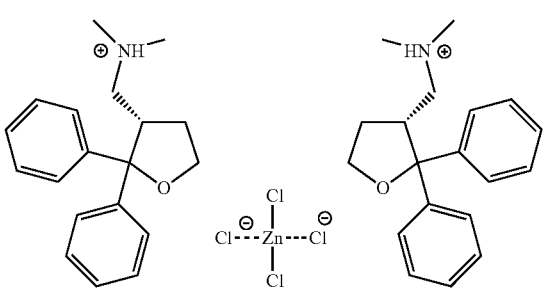

2a

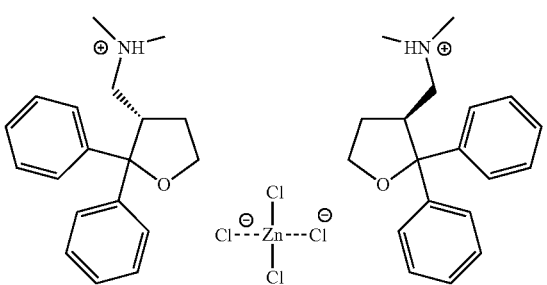

2b

-continued

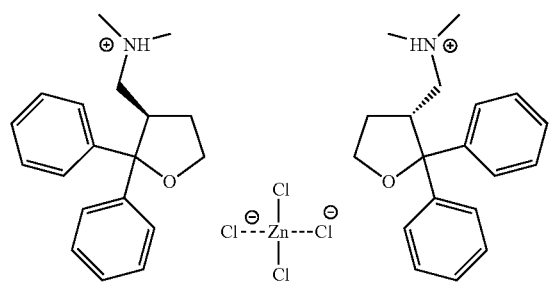

2c

Further aspect of our invention is the process for preparation of said co-crystals.

Further aspect of our invention is the pharmaceutical preparation comprising co-crystal according to our invention that comprises a therapeutically effective amount of co-crystal selected from formula 2a, 2b or 2c and one or more pharmaceutically acceptable excipients selected from filler, diluent, disintegrant, wetting agent, anti-adhesive agent, binder and other excipients commonly used in medicine.

Further aspect of our invention is the process for preparation of said pharmaceutical preparation.

Further aspect of our invention is the use of co-crystal or a pharmaceutical composition containing co-crystal according to our invention in the treatment of neurodegenerative, neurodevelopmental diseases such as Alzheimer's disease, Parkinson's disease dementia and/or Rett syndrome.

Further aspect of our invention is the treatment of neurodegenerative, neurodevelopmental diseases such as Alzheimer's disease, Parkinson's disease dementia and/or Rett syndrome by administering a therapeutically effective amount of co-crystal or a medicinal product containing co-crystal according to our invention to the patient in need of treatment.

DETAILED DESCRIPTION OF THE INVENTION

The aim of our invention was achieved in the following way.

At first, we produced the racemic and optically active blarcamesine bases and their hydrochloric acid salts according to the process below, disclosed in the International Publication WO 9730983 and WO 2013008044 of Anavex:

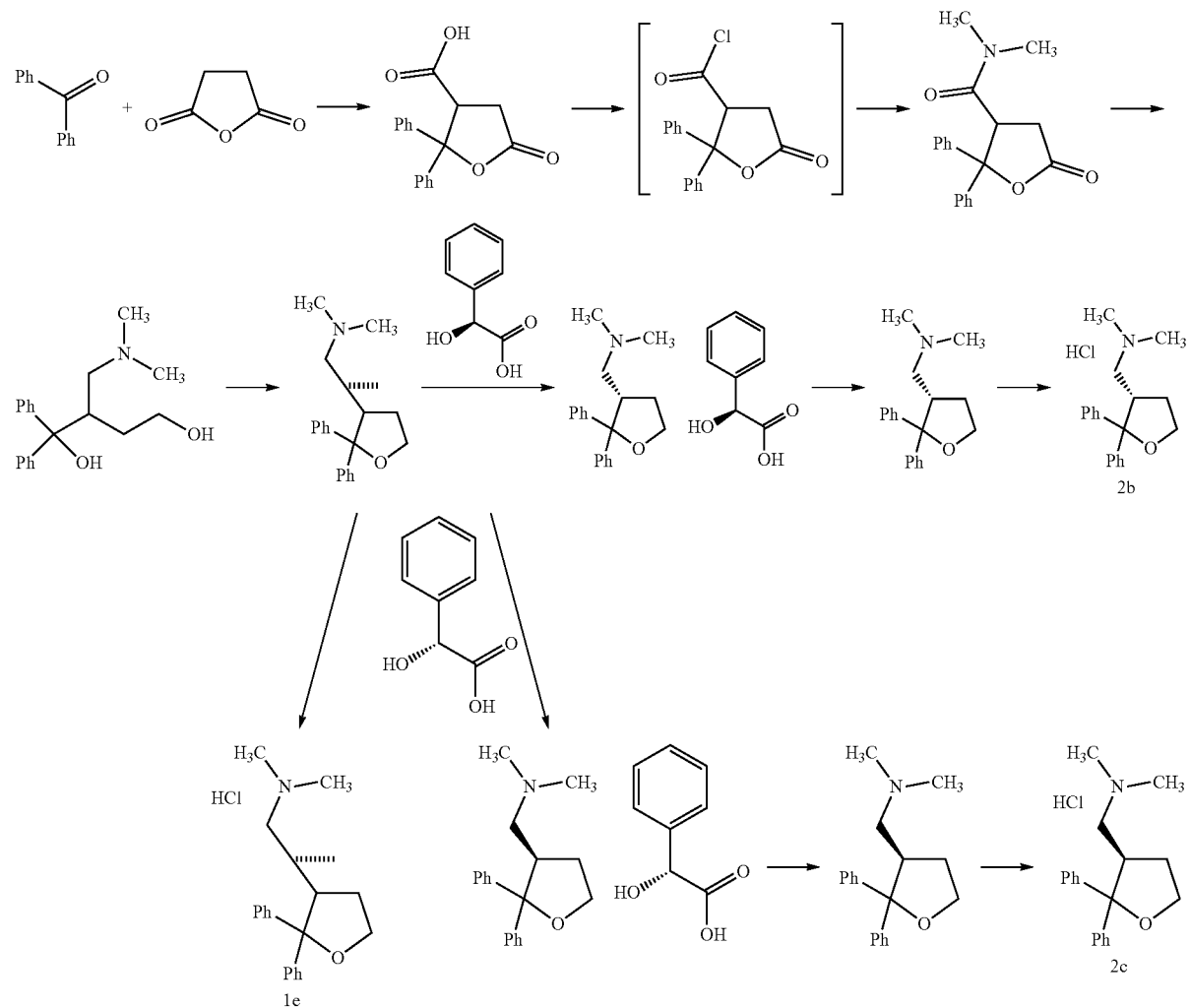

It is known that certain nitrogen-containing organic compounds having aromatic rings form well-crystallizing solid forms in the presence of inorganic salts.

Suitable inorganic salts can be found in several elements of the periodic table, such as the d group. In order to obtain a pharmaceutically acceptable form we had to choose an inorganic salt that is suitable for human use. Therefore Zn—, Mg—, Ca— compounds were investigated, and finally Zn, more precisely $ZnCl_2$, was chosen.

A $ZnCl_2$ solution was added to the solution of racemic blarcamesine base with ether or alcohol and it was found that solid product was precipitated while standing.

Upon examining the solid product, we surprisingly found that the precipitated form was a co-crystal of the hydrochloric salt of blarcamesine with $ZnCl_2$ in a 2:1 molar ratio per unit cell.

The same solid form was also obtained from solutions of blarcamesine hydrochloride and $ZnCl_2$.

We then focused on producing co-crystal with good reproducibility, robustness, and good chemical yield, and characterizing the resulting product.

As a result, we obtained the co-crystal by adding first $ZnCl_2$ and then hydrochloric acid solution to the mixture of the last chemical step of the process disclosed in the International Publication of WO 9730983 and WO 2013008044, without isolating of the racemic blarcamesine base, and finally filtering the product.

The process was carried out in organic solvent or mixtures thereof, which may be aprotic or protic, aromatic solvent, ether, or alcohol, preferably toluene, tetrahydrofuran (THF) or isopropyl alcohol (IPA), and mixtures thereof.

The temperature was between room temperature to 100° C., preferably between 70 and 80° C.

The properties of the isolated solid form were the same in all cases.

The chemical composition and physicochemical properties of the co-crystals were characterized by the following analytical methods: HPLC, ICP, 1H-NMR, 13C-NMR, COSY, HSQC, HMBC, elemental analysis, complexometric titration, SC-XRD, TG, DVS, DSC, XRPD.

Other properties of the of co-crystal were also investigated and compared with those of blarcamesine hydrochloride acid salt.

Surprisingly, we found that the $ZnCl_2$ co-crystal was more resistant to oxidative stress than the hydrochloric acid salt.

We also surprisingly found that the $ZnCl_2$ co-crystal retains its crystal structure after subjecting to wet grinding, whereas the polymorphic form of the hydrochloride salt changes under the same conditions.

As a further beneficial property, we found that the solubility of the $ZnCl_2$ co-crystal is excellent over the entire relevant pH range, but surprisingly much worse than the extreme solubility of the hydrochloric acid salt, which could be an advantageous feature both in the drug formulation technology process and in the potential implementation of a modified release formulation.

Based on the knowledge and experience with the racemic co-crystal, the corresponding optically active $ZnCl_2$ co-crystals were also successfully prepared from (S)-(−)- and (R)-(+)-blarcamesine bases, which were characterized in a similar way as described above.

We carried out our experiments to prepare further co-crystals of the hydrogen halide salt of blarcamesine with Zn halide.

Therefore, we first prepared the racemic blarcamesine hydrobromide of formula 1d (as disclosed in International Publication of TEVA, WO 2021158586, Form A) and successfully prepared the racemic-(±)-blarcamesine hydrobromide $ZnBr_2$ (2:1 per unit cell) co-crystal of formula 2d in a similar way as described for the $ZnCl_2$ co-crystal.

The structure of the obtained solid form was confirmed by both powder and single-crystal X-ray diffraction studies.

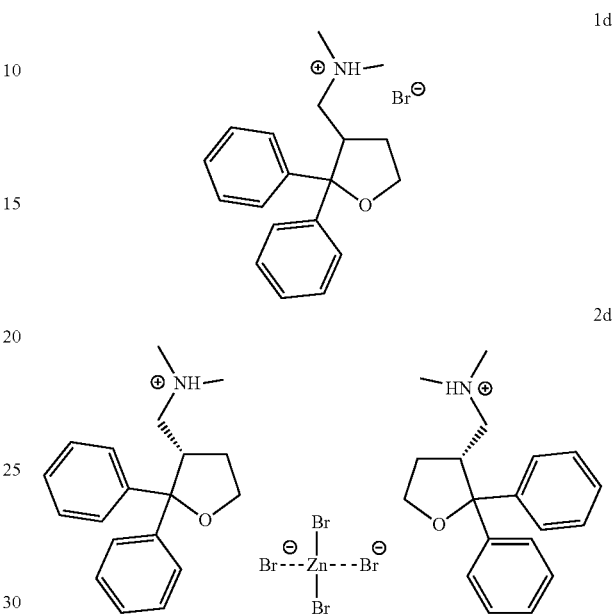

The single crystals prepared from the racemic-(±)-, (S)-(−)- and (R)-(+)-hydrochloride salts of structures 1a, 1b, 1c, 2a, 2b, and 2c respectively, furthermore the co-crystals formed from these salts with zinc chloride were measured with single-crystal X-ray diffractometry. Similarly, we investigated the single crystals of the racemic-(±)-blarcamesine hydrobromide salt of structure 1d and the co-crystal formed from this with zinc bromide. The results are summarized in Table 1. and Table 2.:

TABLE 1

Crystal parameters

| Compound | Space group | Cell constants | Density [kg/m³] | N⁺ ↔ Cl⁻ distance [nm] |
|---|---|---|---|---|
| 1a | P2$_1$/a | a = 1.3527 nm<br>b = 0.9182 nm<br>c = 1.4247 nm<br>β = 102.14° | 1220 | 0.302 |
| 1b | P2$_1$2$_1$2$_1$ | a = 0.7144 nm<br>b = 1.4372 nm<br>c = 1.7325 nm | 1187 | 0.303 |
| 1c | P2$_1$2$_1$2$_1$ | a = 0.7141 nm<br>b = 1.4367 nm<br>c = 1.7316 nm | 1188 | 0.301 |
| 2a | P2$_1$2$_1$2$_1$ | a = 1.5685 nm<br>b = 1.5757 nm<br>c = 1.6045 nm | 1293 | 0.320 |
| 2b | P2$_1$2$_1$2$_1$ | a = 0.8920 nm<br>b = 1.3656 nm<br>c = 3.2538 nm | 1294 | 0.321 |
| 2c | P2$_1$2$_1$2$_1$ | a = 0.8910 nm<br>b = 1.3642 nm<br>c = 3.2533 nm | 1297 | 0.323 |

TABLE 2

Crystal parameters

| Compound | Space group | Cell constants | Density [kg/m³] | N⁺ ↔ Br⁻ distance [nm] |
|---|---|---|---|---|
| 1d | P2$_1$/a | a = 1.4021 nm<br>b = 0.9219 nm<br>c = 1.4212 nm<br>β = 102.34° | 1341 | 0.316 |
| 2d | P2$_1$2$_1$2$_1$ | a = 1.5438 nm<br>b = 1.6018 nm<br>c = 1.6581 nm | 1539 | 0.337 |

We deduced two conclusions from the results measured by single-crystal X-ray diffraction, on one hand the co-crystals formed with zinc chloride differ from the starting hydrochloride salts without any doubt, on the other hand based on the N+.↔. Cl⁻ distance the relation of the protonated ammonium group and the chloride ion did not change relevantly, which supports that really co-crystals were formed. Similarly, the co-crystal formed from the hydrobromide salt with zinc bromide differs without doubt from the starting hydrobromide salt and based on the N⁺.↔.Br⁻ distance the relation between the protonated ammonium group and the bromide ion did not change relevantly, so in this case also a co-crystal was formed.

Figure 1:
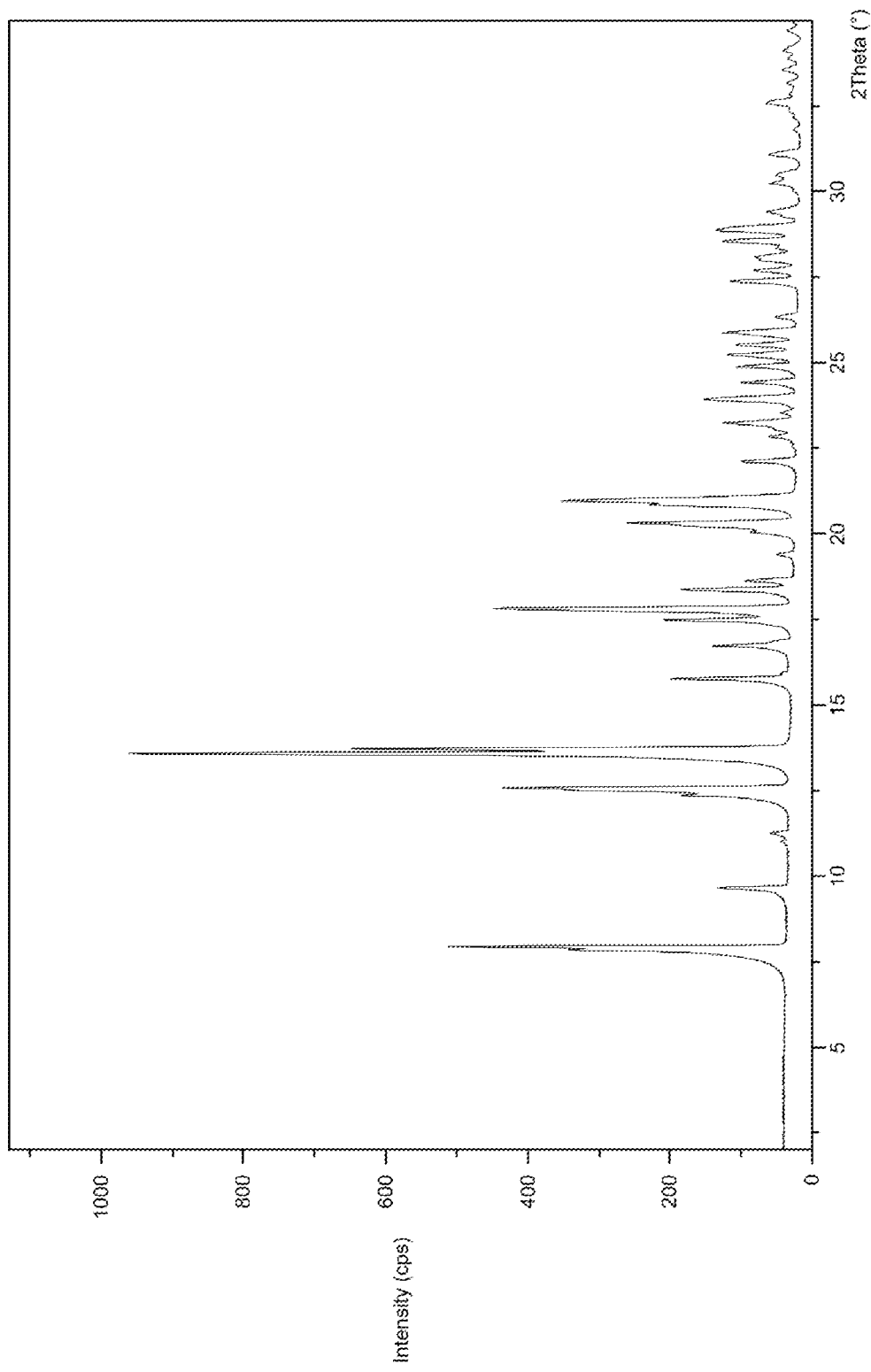
FIG. 1: Experimental X-ray powder diffractogram of (S)-(−)-blarcamesine hydrochloride, (R)-(+)-blarcamesine hydrochloride, $ZnCl_2$ (1:1:1) co-crystal (2a)

Characteristic X-ray powder diffraction peaks of (S)-(−)-blarcamesine hydrochloride, (R)-(+)-blarcamesine hydrochloride, ZnCl$_2$ (1:1:1 per unit cell) co-crystal (2a) are the following: 2θ(±0.2° 2θ): 7.93; 9.66; 17.82. More specifically it may be characterized by the following X-ray powder diffraction peaks: 2θ(±0.2° 2θ): 7.93; 9.66; 13.73; 15.77; 16.73; 17.82. Even more specifically it may be characterized by the following X-ray powder diffraction peaks: 2θ(±0.2° 2θ): 7.84; 7.93; 9.66; 11.25; 12.35; 12.49; 12.58; 13.58; 13.73; 15.77; 16.73; 16.84; 17.48; 17.82; 18.37; 18.63; 19.40; 20.04; 20.23; 20.32; 20.83; 20.96; 21.07; 22.11; 22.83; 23.04; 23.23; 23.91; 24.42; 24.88; 25.23; 25.51; 25.88; 26.32; 27.37; 27.69; 27.98; 28.10; 28.33; 28.54; 28.86; 29.41; 30.23; 30.47; 31.07; 32.33; 32.56; 32.86; 33.17; 33.55; 33.88; 34.10; 34.66. The characteristic X-ray powder diffractogram of (S)-(−)-blarcamesine hydrochloride, (R)-(+)-blarcamesine hydrochloride, ZnCl$_2$ (1:1:1) co-crystal (2a) may be seen in FIG. 1., and the 2% or greater intensity peaks are summarized in Table 3.

TABLE 3

The X-ray powder diffraction data of (S)-(−)-blarcamesine hydrochloride, (R)-(+)-blarcamesine hydrochloride, ZnCl$_2$ (1:1:1) co-crystal (relative intensities ≥ 2%)

| Peak No. | 2θ (°) | d (Å) | Relative intensity (%) |
|---|---|---|---|
| 1 | 7.84 | 11.27 | 26 |
| 2 | 7.93 | 11.15 | 43 |
| 3 | 9.66 | 9.15 | 11 |
| 4 | 11.25 | 7.86 | 3 |
| 5 | 12.35 | 7.17 | 16 |
| 6 | 12.49 | 7.09 | 19 |
| 7 | 12.58 | 7.04 | 31 |
| 8 | 13.58 | 6.52 | 100 |
| 9 | 13.73 | 6.45 | 52 |
| 10 | 15.77 | 5.62 | 17 |
| 11 | 16.73 | 5.30 | 13 |
| 12 | 16.84 | 5.26 | 2 |
| 13 | 17.48 | 5.07 | 19 |
| 14 | 17.82 | 4.98 | 56 |
| 15 | 18.37 | 4.83 | 17 |
| 16 | 18.63 | 4.76 | 8 |
| 17 | 19.40 | 4.58 | 3 |
| 18 | 20.04 | 4.43 | 7 |
| 19 | 20.23 | 4.39 | 13 |
| 20 | 20.32 | 4.37 | 19 |
| 21 | 20.83 | 4.26 | 20 |
| 22 | 20.96 | 4.24 | 32 |
| 23 | 21.07 | 4.22 | 11 |
| 24 | 22.11 | 4.02 | 9 |
| 25 | 22.83 | 3.89 | 4 |
| 26 | 23.04 | 3.86 | 3 |
| 27 | 23.23 | 3.83 | 15 |
| 28 | 23.91 | 3.72 | 19 |
| 29 | 24.42 | 3.64 | 9 |
| 30 | 24.88 | 3.58 | 10 |
| 31 | 25.23 | 3.53 | 13 |
| 32 | 25.51 | 3.49 | 10 |
| 33 | 25.88 | 3.44 | 16 |
| 34 | 26.32 | 3.39 | 4 |
| 35 | 27.37 | 3.26 | 12 |
| 36 | 27.69 | 3.22 | 7 |
| 37 | 27.98 | 3.19 | 5 |
| 38 | 28.10 | 3.18 | 7 |
| 39 | 28.33 | 3.15 | 3 |
| 40 | 28.54 | 3.13 | 14 |
| 41 | 28.86 | 3.09 | 21 |
| 42 | 29.41 | 3.04 | 6 |
| 43 | 30.23 | 2.96 | 5 |
| 44 | 30.47 | 2.93 | 6 |
| 45 | 31.07 | 2.88 | 7 |
| 46 | 32.33 | 2.77 | 2 |
| 47 | 32.56 | 2.75 | 9 |
| 48 | 32.86 | 2.73 | 2 |
| 49 | 33.17 | 2.70 | 4 |
| 50 | 33.55 | 2.67 | 5 |

TABLE 3-continued

The X-ray powder diffraction data of (S)-(-)-blarcamesine hydrochloride, (R)-(+)-blarcamesine hydrochloride, ZnCl₂ (1:1:1) co-crystal (relative intensities ≥ 2%)

| Peak No. | 2θ (°) | d (Å) | Relative intensity (%) |
|---|---|---|---|
| 51 | 33.88 | 2.65 | 4 |
| 52 | 34.10 | 2.63 | 4 |
| 53 | 34.66 | 2.59 | 6 |

Figure 2:
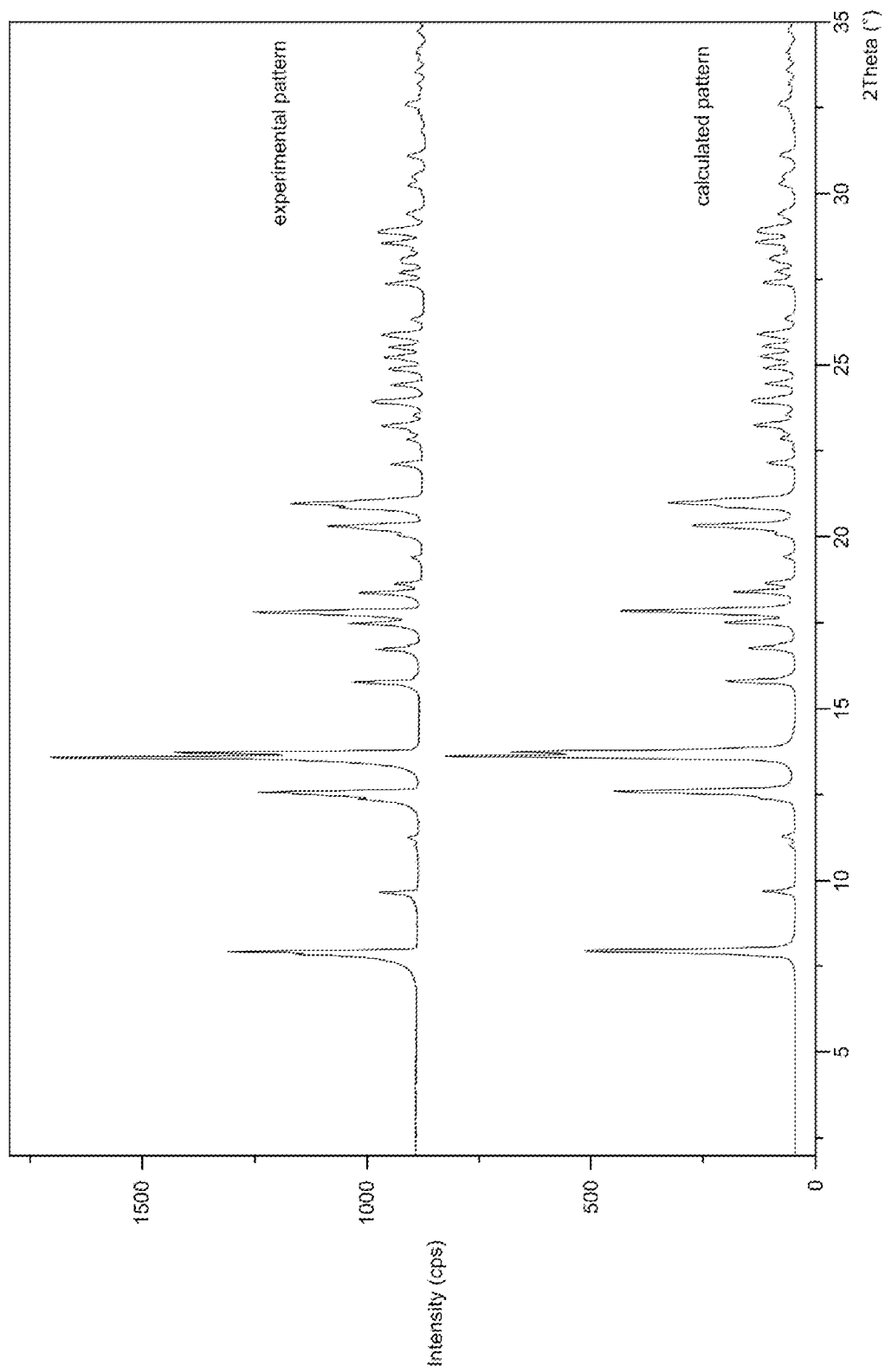
FIG. 2: Experimental and calculated X-ray powder diffractograms of (S)-(−)-blarcamesine hydrochloride, (R)-(+)-blarcamesine hydrochloride, $ZnCl_2$ (1:1:1) co-crystal (2a)

With single crystal X-ray diffraction, the exact atomic positions can be determined in the crystal. Based on these data, the powder X-ray diffraction pattern can be calculated. Experimental and calculated powder X-ray diffraction patterns of (S)-(-)-blarcamesine hydrochloride, (R)-(+)-blarcamesine hydrochloride, ZnCl₂ (1:1:1) co-crystal (2a) are identical (FIG. 2.), therefore the presented crystal phase is pure and uniform.

Figure 3:
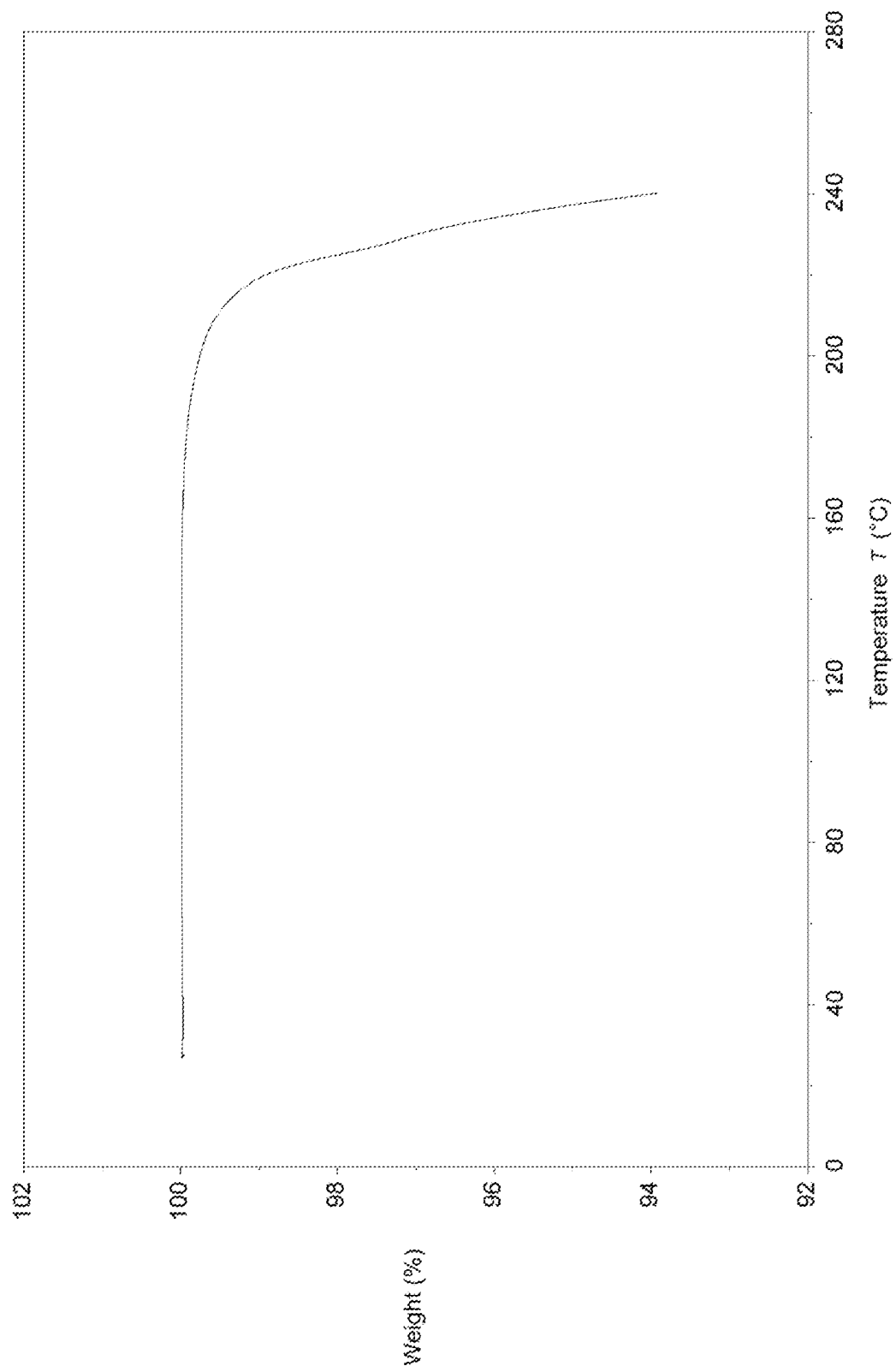
FIG. 3: TGA-thermogram of (S)-(−)-blarcamesine hydrochloride, (R)-(+)-blarcamesine hydrochloride, $ZnCl_2$ (1:1:1) co-crystal (2a)
Figure 4:
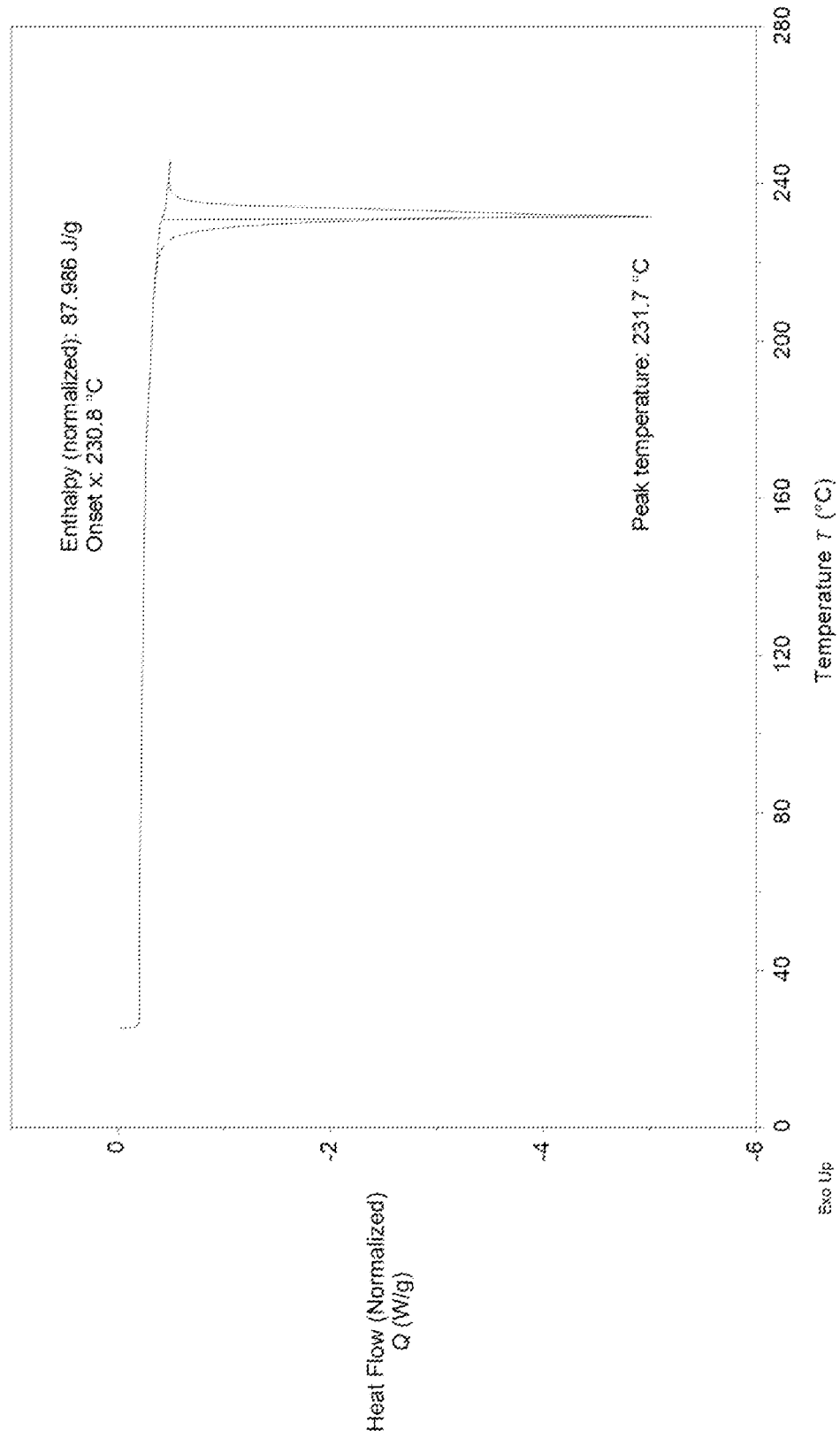
FIG. 4: DSC-thermogram of (S)-(−)-blarcamesine hydrochloride, (R)-(+)-blarcamesine hydrochloride, $ZnCl_2$ (1:1:1) co-crystal (2a)
Figure 5:
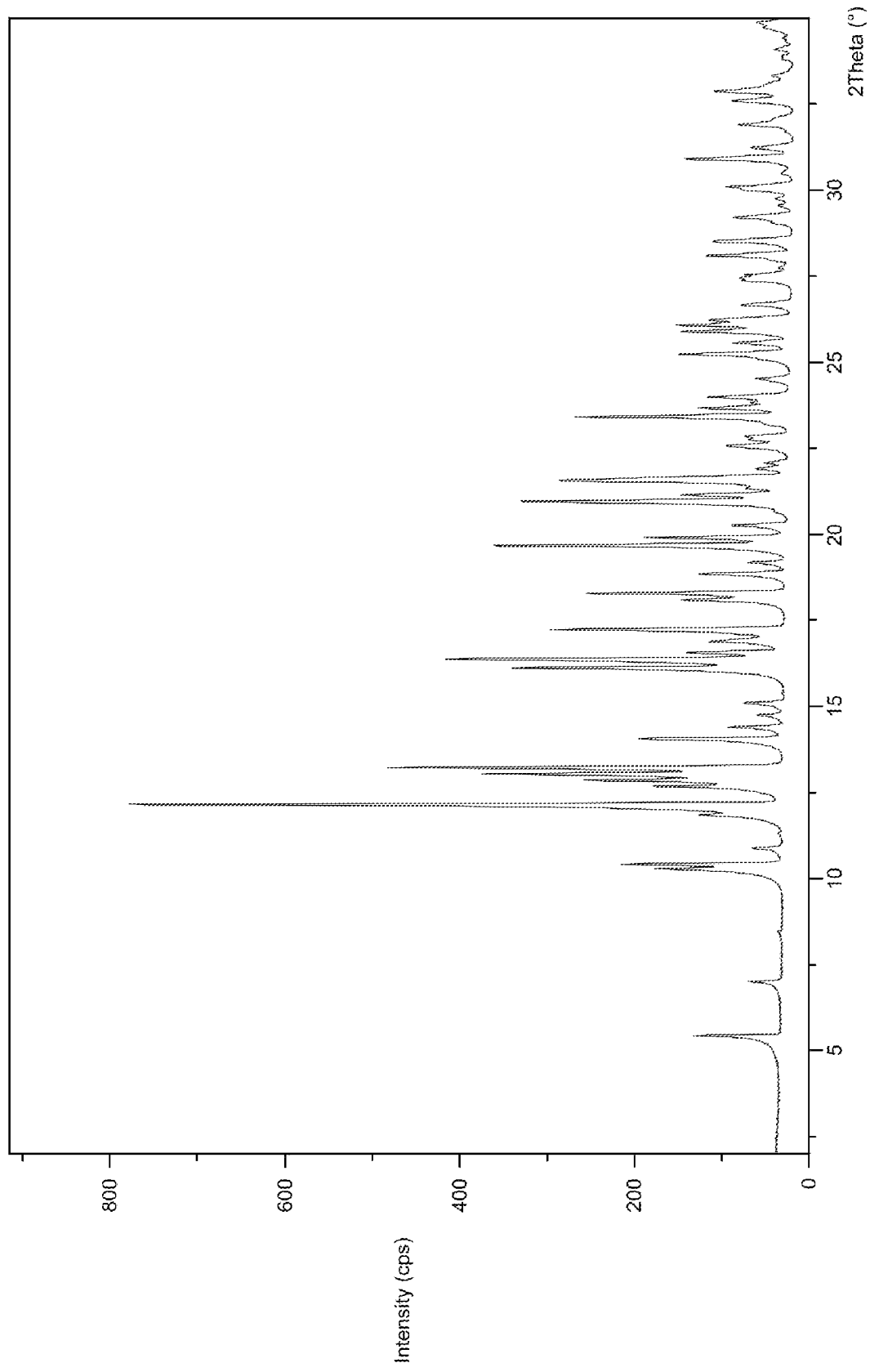
FIG. 5: Experimental X-ray powder diffractogram of (S)-(−)-blarcamesine hydrochloride, $ZnCl_2$ (2:1) co-crystal (2b)

Based on the results of TGA (thermogravimetric analysis) measurements it can be stated that (S)-(-)-blarcamesine hydrochloride, (R)-(+)-blarcamesine hydrochloride, ZnCl₂ (1:1:1) co-crystal (2a) is a water and solvent free (anhydrous) form (amount of volatile compounds evaporated from the sample stayed below 0.1% w/w until reaching the temperature value of 160° C., FIG. 3.) Based on DSC (differential scanning calorimetry) measurement the melting onset temperature of the presented crystal phase is 230-231° C. (FIG. 4.) Characteristic X-ray powder diffraction peaks of (S)-(-)-blarcamesine hydrochloride, ZnCl₂ (2:1 per unit cell) co-crystal (2b) are the following: 2θ(±0.20 2θ): 12.15; 13.04; 19.67. More specifically it may be characterized by the following X-ray powder diffraction peaks: 2θ(±0.20 2θ): 12.15; 12.85; 13.04; 13.24; 16.36; 19.67. Even more specifically it may be characterized by the following X-ray powder diffraction peaks: 2θ(±0.2 2θ): 5.44; 7.02; 10.28; 10.41; 10.89; 11.82; 12.15; 12.67; 12.85; 13.04; 13.23; 14.05; 14.40; 14.75; 15.09; 16.11; 16.36; 16.56; 16.87; 17.23; 18.09; 18.28; 18.84; 19.17; 19.67; 19.90; 20.25; 20.94; 21.14; 21.34; 21.55; 21.90; 22.07; 22.56; 22.74; 22.85; 23.20; 23.41; 23.67; 23.98; 24.52; 25.22; 25.55; 25.88; 26.07; 26.22; 26.66; 27.39; 27.54; 27.75; 28.10; 28.51; 29.05; 29.20; 29.54; 29.74; 30.00; 30.09; 30.48; 30.90; 31.23; 31.90; 32.04; 32.58; 32.86; 33.32; 33.81; 34.08; 34.71; 34.88. The characteristic X-ray powder diffractogram of (S)-(-)-blarcamesine hydrochloride, ZnC₂ (2:1) co-crystal (2b) may be seen in FIG. 5., and the 2% or greater intensity peaks are summarized in Table 4.

TABLE 4

The X-ray powder diffraction data of (S)-(-)-blarcamesine hydrochloride, ZnCl₂ (2:1) co-crystal (relative intensities ≥ 2%)

| Peak No. | 2θ (°) | d (Å) | Relative intensity (%) |
|---|---|---|---|
| 1 | 5.44 | 16.24 | 17 |
| 2 | 7.02 | 12.60 | 6 |
| 3 | 10.28 | 8.60 | 24 |
| 4 | 10.41 | 8.49 | 20 |
| 5 | 10.89 | 8.12 | 6 |
| 6 | 11.82 | 7.49 | 15 |
| 7 | 12.15 | 7.29 | 100 |
| 8 | 12.67 | 6.98 | 19 |
| 9 | 12.85 | 6.89 | 26 |
| 10 | 13.04 | 6.79 | 41 |
| 11 | 13.23 | 6.69 | 62 |
| 12 | 14.05 | 6.30 | 24 |
| 13 | 14.40 | 6.15 | 9 |
| 14 | 14.75 | 6.01 | 5 |
| 15 | 15.09 | 5.87 | 8 |
| 16 | 16.11 | 5.50 | 40 |
| 17 | 16.36 | 5.42 | 60 |
| 18 | 16.56 | 5.35 | 16 |
| 19 | 16.87 | 5.25 | 17 |
| 20 | 17.23 | 5.15 | 39 |
| 21 | 18.09 | 4.90 | 16 |
| 22 | 18.28 | 4.85 | 32 |
| 23 | 18.84 | 4.71 | 15 |
| 24 | 19.17 | 4.63 | 5 |
| 25 | 19.67 | 4.51 | 46 |
| 26 | 19.90 | 4.46 | 23 |
| 27 | 20.25 | 4.39 | 10 |
| 28 | 20.94 | 4.24 | 42 |
| 29 | 21.14 | 4.20 | 16 |
| 30 | 21.34 | 4.16 | 4 |
| 31 | 21.55 | 4.12 | 56 |
| 32 | 21.90 | 4.06 | 4 |
| 33 | 22.07 | 4.03 | 3 |
| 34 | 22.56 | 3.94 | 13 |
| 35 | 22.74 | 3.91 | 5 |
| 36 | 22.85 | 3.89 | 5 |
| 37 | 23.20 | 3.83 | 2 |
| 38 | 23.41 | 3.80 | 34 |
| 39 | 23.67 | 3.76 | 16 |
| 40 | 23.98 | 3.71 | 15 |
| 41 | 24.52 | 3.63 | 6 |
| 42 | 25.22 | 3.53 | 18 |
| 43 | 25.55 | 3.49 | 9 |
| 44 | 25.88 | 3.44 | 18 |
| 45 | 26.07 | 3.42 | 16 |
| 46 | 26.22 | 3.40 | 16 |
| 47 | 26.66 | 3.34 | 10 |
| 48 | 27.39 | 3.26 | 12 |
| 49 | 27.54 | 3.24 | 5 |
| 50 | 27.75 | 3.21 | 2 |
| 51 | 28.10 | 3.18 | 14 |
| 52 | 28.51 | 3.13 | 16 |
| 53 | 29.05 | 3.07 | 3 |
| 54 | 29.20 | 3.06 | 11 |
| 55 | 29.54 | 3.02 | 3 |
| 56 | 29.74 | 3.00 | 2 |
| 57 | 30.00 | 2.98 | 7 |
| 58 | 30.09 | 2.97 | 10 |
| 59 | 30.48 | 2.93 | 2 |
| 60 | 30.90 | 2.89 | 21 |
| 61 | 31.23 | 2.86 | 10 |
| 62 | 31.90 | 2.81 | 10 |
| 63 | 32.04 | 2.79 | 3 |
| 64 | 32.58 | 2.75 | 13 |
| 65 | 32.86 | 2.73 | 22 |
| 66 | 33.32 | 2.69 | 4 |
| 67 | 33.81 | 2.65 | 3 |
| 68 | 34.08 | 2.63 | 3 |
| 69 | 34.71 | 2.58 | 6 |
| 70 | 34.88 | 2.57 | 9 |

Figure 6:
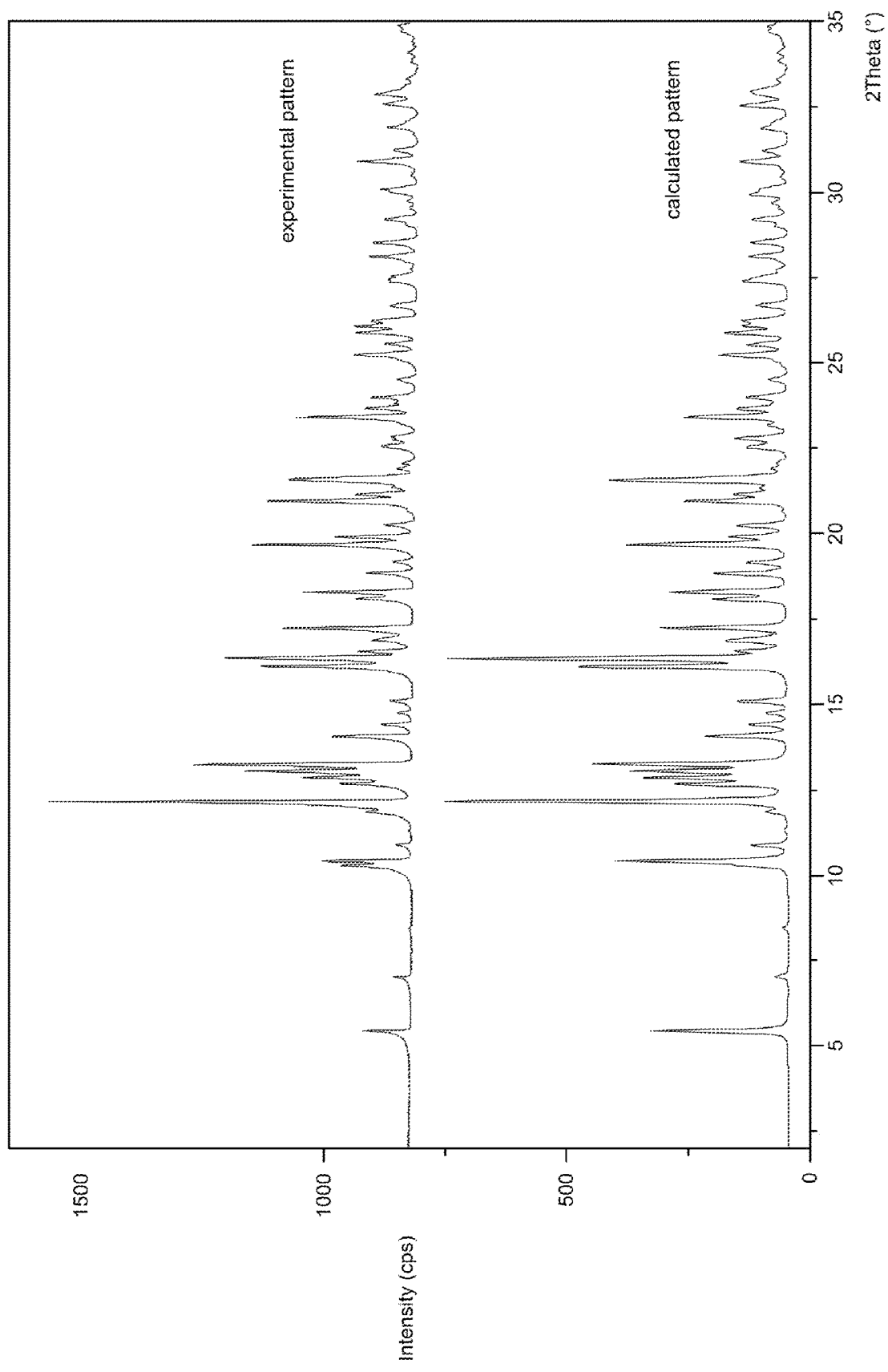
FIG. 6: Experimental and calculated X-ray powder diffractograms of (S)-(−)-blarcamesine hydrochloride, $ZnCl_2$ (2:1) co-crystal (2b)

With single crystal X-ray diffraction, the exact atomic positions can be determined in the crystal. Based on these data, the powder X-ray diffraction pattern can be calculated. Experimental and calculated powder X-ray diffraction patterns of (S)-(-)-blarcamesine hydrochloride, ZnCl₂ (2:1) co-crystal (2b) are identical (FIG. 6.), therefore the presented crystal phase is pure and uniform.

Figure 7:
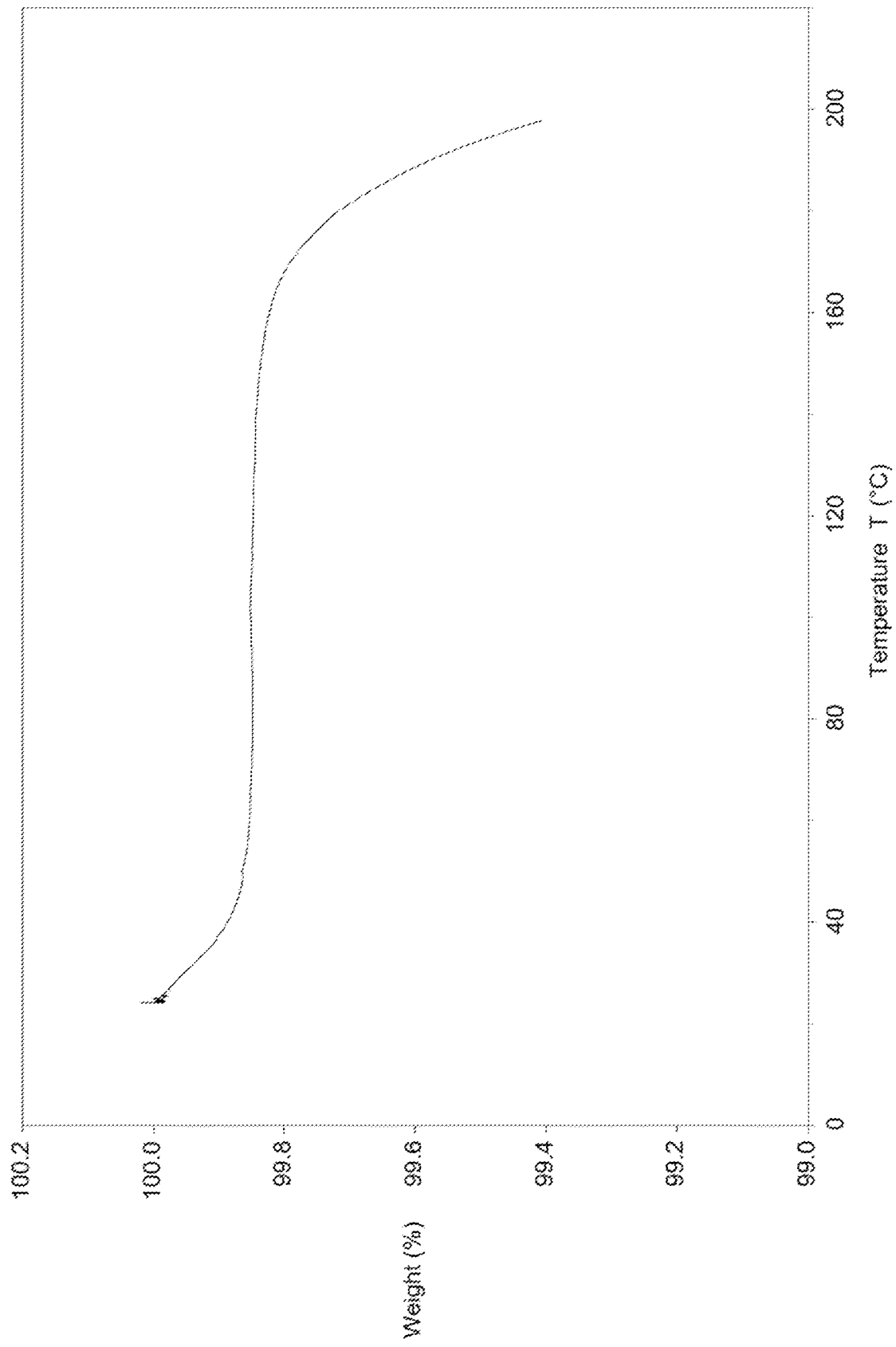
FIG. 7: TGA-thermogram of (S)-(−)-blarcamesine hydrochloride, $ZnCl_2$ (2:1) co-crystal (2b)
Figure 8:
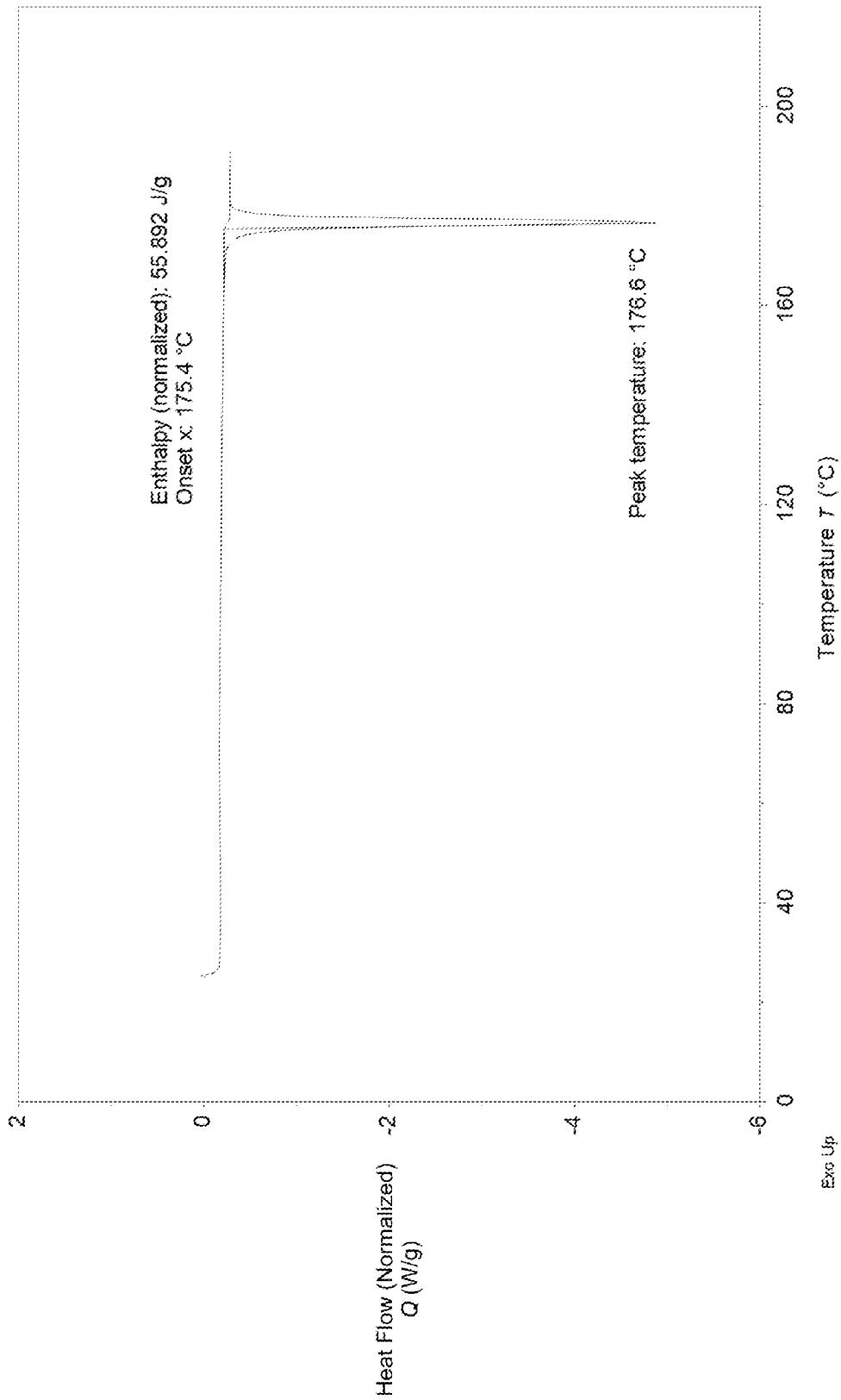
FIG. 8: DSC-thermogram of (S)-(−)-blarcamesine hydrochloride, $ZnCl_2$ (2:1) co-crystal (2b)

Based on the results of TGA (thermogravimetric analysis) measurements it can be stated that (S)-(-)-blarcamesine hydrochloride, ZnCl₂ (2:1) co-crystal (2b) is a water and solvent free (anhydrous) form (amount of volatile compounds evaporated from the sample stayed below 0.5% w/w until reaching the temperature value of 120° C., FIG. 7.) Based on DSC (differential scanning calorimetry) measurement the melting onset temperature of the presented crystal phase is 175-176° C. (FIG. 8.)

Figure 9:
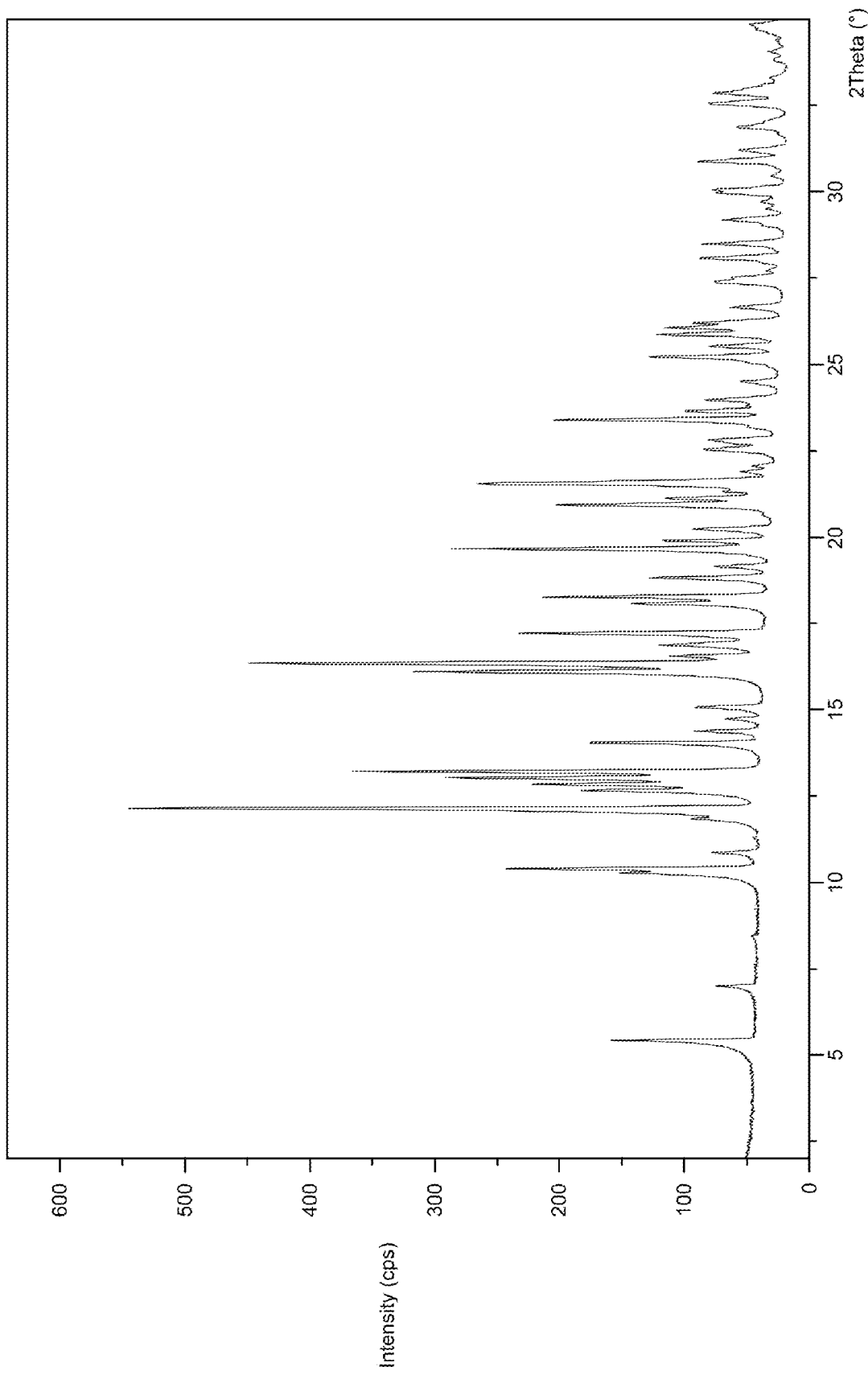
FIG. 9: Experimental X-ray powder diffractogram of (R)-(+)-blarcamesine hydrochloride, $ZnCl_2$ (2:1) co-crystal (2c)

Characteristic X-ray powder diffraction peaks of (R)-(+)-blarcamesine hydrochloride, $ZnCl_2$ (2:1 per unit cell) co-crystal (2c) are the following: 2θ(±0.2° 2θ): 12.15; 13.04; 19.67. More specifically it may be characterized by the following X-ray powder diffraction peaks: 2θ(±0.2° 2θ): 12.15; 12.85; 13.04; 13.24; 16.36; 19.67. Even more specifically it may be characterized by the following X-ray powder diffraction peaks: 2θ(±0.2° 2θ): 5.43; 7.01; 10.27; 10.40; 10.87; 11.82; 12.15; 12.65; 12.85; 13.04; 13.24; 14.04; 14.38; 14.73; 15.07; 16.09; 16.36; 16.54; 16.85; 17.21; 18.07; 18.27; 18.81; 19.14; 19.67; 19.88; 20.23; 20.93; 21.13; 21.31; 21.52; 21.88; 22.06; 22.53; 22.72; 22.81; 23.17; 23.39; 23.65; 23.97; 24.50; 25.21; 25.52; 25.86; 26.05; 26.20; 26.64; 27.37; 27.52; 27.71; 28.07; 28.48; 29.02; 29.18; 29.52; 29.71; 29.96; 30.07; 30.45; 30.88; 31.20; 31.87; 32.04; 32.54; 32.84; 33.30; 33.79; 34.05; 34.69; 34.85. The characteristic X-ray powder diffractogram of (R)-(+)-blarcamesine hydrochloride, $ZnCl_2$ (2:1) co-crystal (2c) may be seen in FIG. 9., and the 2% or greater intensity peaks are summarized in Table 5. (R)-(+)-blarcamesine hydrochloride, $ZnCl_2$ (2:1) co-crystal and (S)-(−)-blarcamesine hydrochloride, $ZnCl_2$ (2:1) co-crystal have the same X-ray powder diffraction pattern.

TABLE 5

The X-ray powder diffraction data of (R)-(+)-blarcamesine hydrochloride, $ZnCl_2$ (2:1) co-crystal (relative intensities ≥ 2%)

| Peak No. | 2θ (°) | d (Å) | Relative intensity (%) |
|---|---|---|---|
| 1 | 5.43 | 16.29 | 29 |
| 2 | 7.01 | 12.62 | 7 |
| 3 | 10.27 | 8.62 | 21 |
| 4 | 10.40 | 8.51 | 39 |
| 5 | 10.87 | 8.14 | 10 |
| 6 | 11.82 | 7.49 | 11 |
| 7 | 12.15 | 7.29 | 100 |
| 8 | 12.65 | 7.00 | 26 |
| 9 | 12.84 | 6.90 | 33 |
| 10 | 13.04 | 6.80 | 48 |
| 11 | 13.24 | 6.70 | 64 |
| 12 | 14.04 | 6.31 | 30 |
| 13 | 14.38 | 6.16 | 12 |
| 14 | 14.73 | 6.01 | 7 |
| 15 | 15.07 | 5.88 | 14 |
| 16 | 16.09 | 5.51 | 55 |
| 17 | 16.34 | 5.43 | 93 |
| 18 | 16.54 | 5.36 | 17 |
| 19 | 16.85 | 5.26 | 24 |
| 20 | 17.21 | 5.15 | 42 |
| 21 | 18.07 | 4.91 | 22 |
| 22 | 18.27 | 4.86 | 36 |
| 23 | 18.81 | 4.72 | 20 |
| 24 | 19.14 | 4.64 | 9 |
| 25 | 19.67 | 4.52 | 50 |
| 26 | 19.88 | 4.47 | 12 |
| 27 | 20.23 | 4.39 | 15 |
| 28 | 20.93 | 4.24 | 38 |
| 29 | 21.13 | 4.21 | 16 |
| 30 | 21.31 | 4.17 | 7 |
| 31 | 21.52 | 4.13 | 70 |
| 32 | 21.88 | 4.06 | 3 |
| 33 | 22.06 | 4.03 | 2 |
| 34 | 22.53 | 3.95 | 14 |
| 35 | 22.72 | 3.91 | 6 |
| 36 | 22.81 | 3.90 | 9 |
| 37 | 23.17 | 3.84 | 3 |
| 38 | 23.39 | 3.80 | 36 |
| 39 | 23.65 | 3.76 | 15 |
| 40 | 23.97 | 3.71 | 20 |
| 41 | 24.50 | 3.63 | 6 |
| 42 | 25.21 | 3.53 | 21 |
| 43 | 25.52 | 3.49 | 12 |
| 44 | 25.86 | 3.45 | 22 |
| 45 | 26.05 | 3.42 | 16 |
| 46 | 26.20 | 3.40 | 17 |
| 47 | 26.64 | 3.35 | 10 |
| 48 | 27.37 | 3.26 | 14 |
| 49 | 27.52 | 3.24 | 6 |
| 50 | 27.71 | 3.22 | 2 |
| 51 | 28.07 | 3.18 | 14 |
| 52 | 28.48 | 3.13 | 15 |
| 53 | 29.02 | 3.08 | 5 |
| 54 | 29.18 | 3.06 | 10 |
| 55 | 29.52 | 3.03 | 3 |
| 56 | 29.71 | 3.01 | 4 |
| 57 | 29.96 | 2.98 | 11 |
| 58 | 30.07 | 2.97 | 11 |
| 59 | 30.45 | 2.94 | 2 |
| 60 | 30.88 | 2.90 | 19 |
| 61 | 31.20 | 2.87 | 11 |
| 62 | 31.87 | 2.81 | 11 |
| 63 | 32.04 | 2.79 | 4 |
| 64 | 32.54 | 2.75 | 18 |
| 65 | 32.84 | 2.73 | 23 |
| 66 | 33.30 | 2.69 | 4 |
| 67 | 33.79 | 2.65 | 4 |
| 68 | 34.05 | 2.63 | 4 |
| 69 | 34.69 | 2.59 | 6 |
| 70 | 34.85 | 2.57 | 11 |

Figure 10:
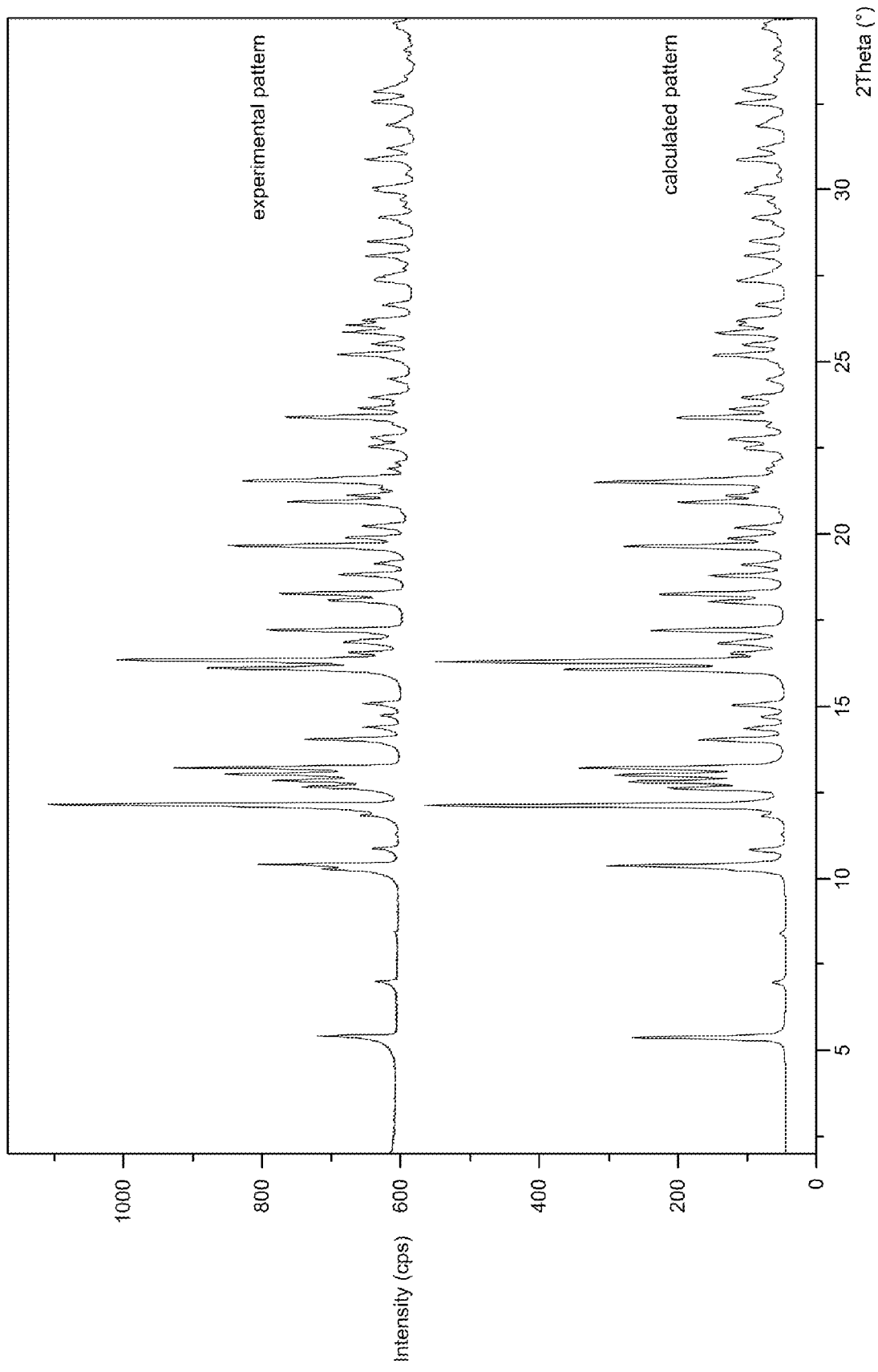
FIG. 10: Experimental and calculated X-ray powder diffractograms of (R)-(+)-blarcamesine hydrochloride, $ZnCl_2$ (2:1) co-crystal (2c)

With single-crystal X-ray diffraction the exact atomic positions can be determined in the crystal. Based on these data, the powder X-ray diffraction pattern can be calculated. Experimental and calculated powder X-ray diffraction patterns of (R)-(+)-blarcamesine hydrochloride, $ZnCl_2$ (2:1) co-crystal (2c) are identical (FIG. 10.), therefore the presented crystal phase is pure and uniform.

Figure 11:
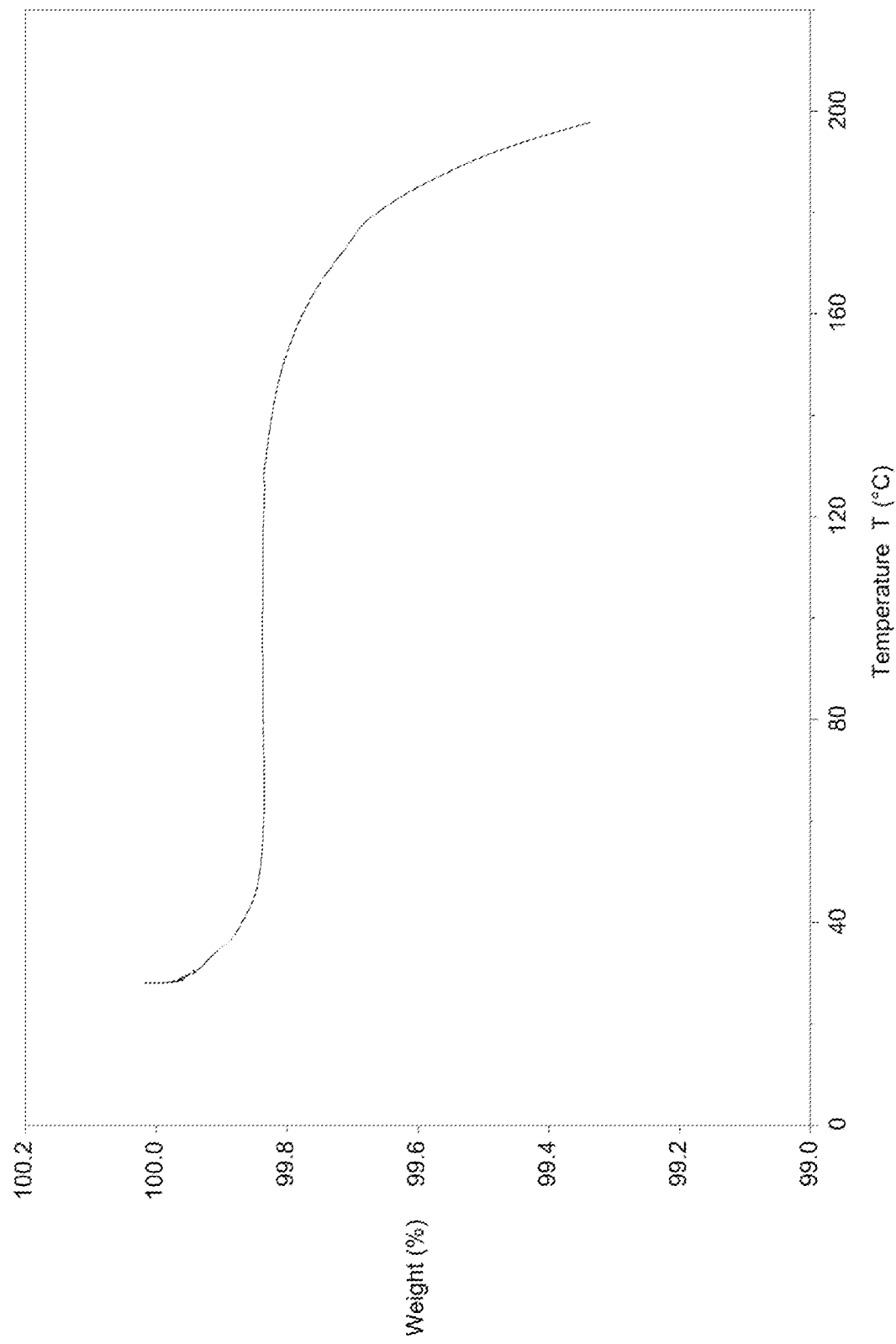
FIG. 11: TGA-thermogram of (R)-(+)-blarcamesine hydrochloride, $ZnCl_2$ (2:1) co-crystal (2c)
Figure 12:
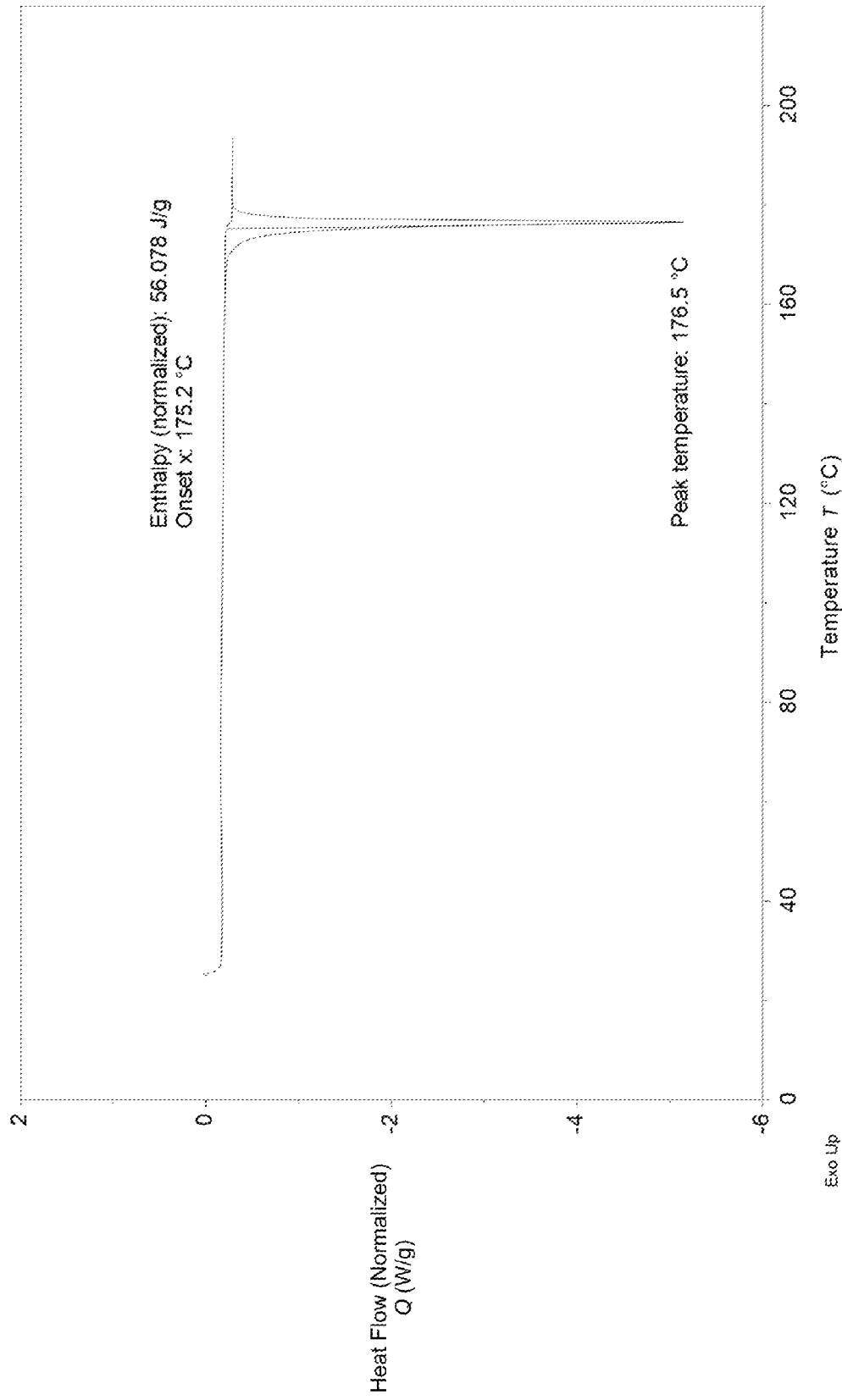
FIG. 12: DSC-thermogram of (R)-(+)-blarcamesine hydrochloride, $ZnCl_2$ (2:1) co-crystal (2c)

Based on the results of TGA (thermogravimetric analysis) measurements it can be stated that (R)-(+)-blarcamesine hydrochloride, $ZnCl_2$ (2:1) co-crystal (2c) is a water and solvent free (anhydrous) form (amount of volatile compounds evaporated from the sample stayed below 0.5% w/w until reaching the temperature value of 120° C., FIG. 11.) Based on DSC (differential scanning calorimetry) measurement the melting onset temperature of the presented crystal phase is 175-176° C. (FIG. 12.)

Figure 13:
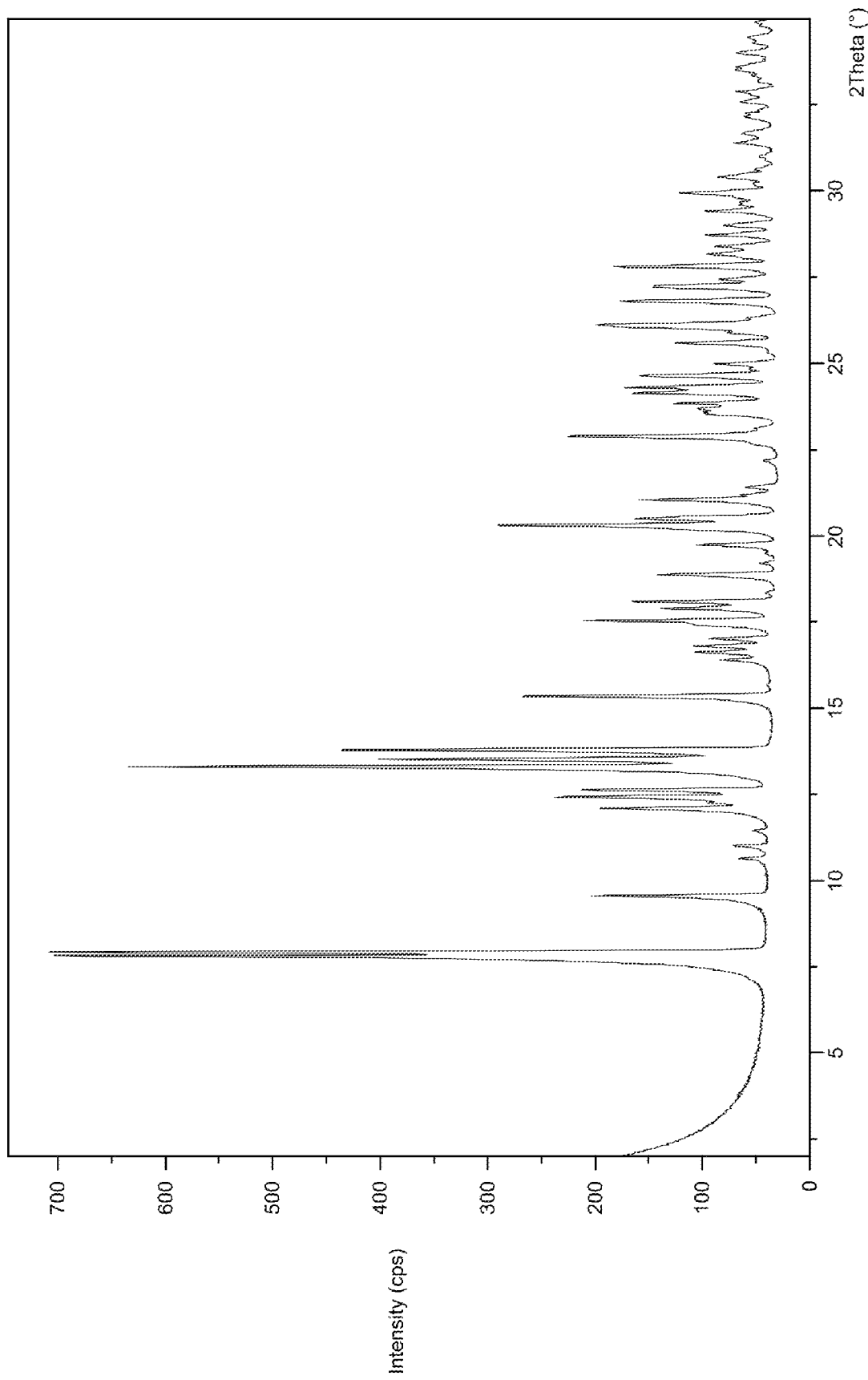
FIG. 13: Experimental X-ray powder diffractogram of (S)-(−)-blarcamesine hydrobromide, (R)-(+)-blarcamesine hydrobromide, ZnBr$_2$ (1:1:1) co-crystal (2d)

Characteristic X-ray powder diffraction peaks of (S)-(−)-blarcamesine hydrobromide, (R)-(+)-blarcamesine hydrobromide, $ZnBr_2$ (1:1:1 per unit cell) co-crystal (2d) are the following: 2θ(±0.2° 2θ): 7.81; 9.57; 13.30. More specifically it may be characterized by the following X-ray powder diffraction peaks: 2θ(±0.2° 2θ): 7.81; 9.57; 13.30; 15.35; 24.30. Even more specifically it may be characterized by the following X-ray powder diffraction peaks: 2θ(±0.2° 2θ): 7.81; 7.93; 9.57; 10.67; 11.02; 11.44; 12.10; 12.23; 12.42; 12.63; 13.30; 13.52; 13.79; 15.35; 16.40; 16.61; 16.79; 17.01; 17.40; 17.53; 17.89; 18.08; 18.86; 19.73; 20.17; 20.30; 20.48; 21.04; 21.18; 21.40; 22.68; 22.88; 23.11; 23.53; 23.68; 23.84; 24.14; 24.30; 24.64; 24.82; 24.98; 25.58; 25.88; 26.04; 26.11; 26.31; 26.80; 27.20; 27.43; 27.81; 28.05; 28.17; 28.39; 28.72; 29.00; 29.41; 29.60; 29.81; 29.94; 30.15; 30.41; 30.64; 31.01; 31.39; 31.65; 32.14; 32.26; 32.58; 32.89; 33.17; 33.35; 33.51; 33.62; 34.00; 34.28; 34.45; 34.78; 34.89. The characteristic X-ray powder diffractogram of (S)-(−)-blarcamesine hydrobromide, (R)-(+)-blarcamesine hydrobromide, ZnBr$_2$ (1:1:1) co-crystal (2d) may be seen in FIG. 13., and the 2% or greater intensity peaks are summarized in Table 6.

TABLE 6

The X-ray powder diffraction data of (S)-(−)-blarcamesine hydrobromide, (R)-(+)-blarcamesine hydrobromide, ZnBr$_2$ (1:1:1) co-crystal (relative intensities ≥ 2%)

| Peak No. | 2θ (°) | d (Å) | Relative intensity (%) |
|---|---|---|---|
| 1 | 7.81 | 11.32 | 100 |
| 2 | 7.93 | 11.15 | 66 |
| 3 | 9.57 | 9.25 | 25 |
| 4 | 10.67 | 8.29 | 10 |
| 5 | 11.02 | 8.03 | 6 |
| 6 | 11.44 | 7.73 | 4 |
| 7 | 12.10 | 7.32 | 23 |
| 8 | 12.23 | 7.23 | 5 |
| 9 | 12.42 | 7.13 | 23 |
| 10 | 12.63 | 7.01 | 21 |
| 11 | 13.30 | 6.66 | 74 |
| 12 | 13.52 | 6.55 | 44 |
| 13 | 13.79 | 6.42 | 52 |
| 14 | 15.35 | 5.77 | 31 |
| 15 | 16.40 | 5.41 | 6 |
| 16 | 16.61 | 5.34 | 9 |
| 17 | 16.79 | 5.28 | 9 |
| 18 | 17.01 | 5.21 | 7 |
| 19 | 17.40 | 5.10 | 8 |
| 20 | 17.53 | 5.06 | 20 |
| 21 | 17.89 | 4.96 | 12 |
| 22 | 18.08 | 4.91 | 16 |
| 23 | 18.86 | 4.70 | 13 |
| 24 | 19.73 | 4.50 | 8 |
| 25 | 20.17 | 4.40 | 7 |
| 26 | 20.30 | 4.38 | 31 |
| 27 | 20.48 | 4.34 | 18 |
| 28 | 21.04 | 4.22 | 17 |
| 29 | 21.18 | 4.19 | 3 |
| 30 | 21.40 | 4.15 | 3 |
| 31 | 22.68 | 3.92 | 3 |
| 32 | 22.88 | 3.89 | 26 |
| 33 | 23.11 | 3.85 | 2 |
| 34 | 23.53 | 3.78 | 9 |
| 35 | 23.68 | 3.76 | 7 |
| 36 | 23.84 | 3.73 | 12 |
| 37 | 24.14 | 3.69 | 15 |
| 38 | 24.30 | 3.66 | 20 |
| 39 | 24.64 | 3.61 | 18 |
| 40 | 24.82 | 3.59 | 2 |
| 41 | 24.98 | 3.57 | 7 |
| 42 | 25.58 | 3.48 | 12 |
| 43 | 25.88 | 3.44 | 3 |
| 44 | 26.04 | 3.42 | 12 |
| 45 | 26.11 | 3.41 | 22 |
| 46 | 26.31 | 3.39 | 3 |
| 47 | 26.80 | 3.33 | 19 |
| 48 | 27.20 | 3.28 | 22 |
| 49 | 27.43 | 3.25 | 5 |
| 50 | 27.81 | 3.21 | 21 |
| 51 | 28.05 | 3.18 | 4 |
| 52 | 28.17 | 3.17 | 10 |
| 53 | 28.39 | 3.14 | 8 |
| 54 | 28.72 | 3.11 | 9 |
| 55 | 29.00 | 3.08 | 8 |
| 56 | 29.41 | 3.04 | 11 |
| 57 | 29.60 | 3.02 | 5 |
| 58 | 29.81 | 3.00 | 5 |
| 59 | 29.94 | 2.98 | 14 |
| 60 | 30.15 | 2.96 | 5 |
| 61 | 30.41 | 2.94 | 10 |
| 62 | 30.64 | 2.92 | 4 |
| 63 | 31.01 | 2.88 | 4 |
| 64 | 31.39 | 2.85 | 9 |
| 65 | 31.65 | 2.83 | 9 |
| 66 | 32.14 | 2.78 | 6 |
| 67 | 32.26 | 2.77 | 8 |
| 68 | 32.58 | 2.75 | 8 |
| 69 | 32.89 | 2.72 | 7 |
| 70 | 33.17 | 2.70 | 5 |
| 71 | 33.35 | 2.69 | 6 |
| 72 | 33.51 | 2.67 | 7 |
| 73 | 33.62 | 2.67 | 5 |
| 74 | 34.00 | 2.64 | 9 |
| 75 | 34.28 | 2.62 | 5 |
| 76 | 34.45 | 2.60 | 8 |
| 77 | 34.78 | 2.58 | 4 |
| 78 | 34.89 | 2.57 | 5 |

Figure 14:
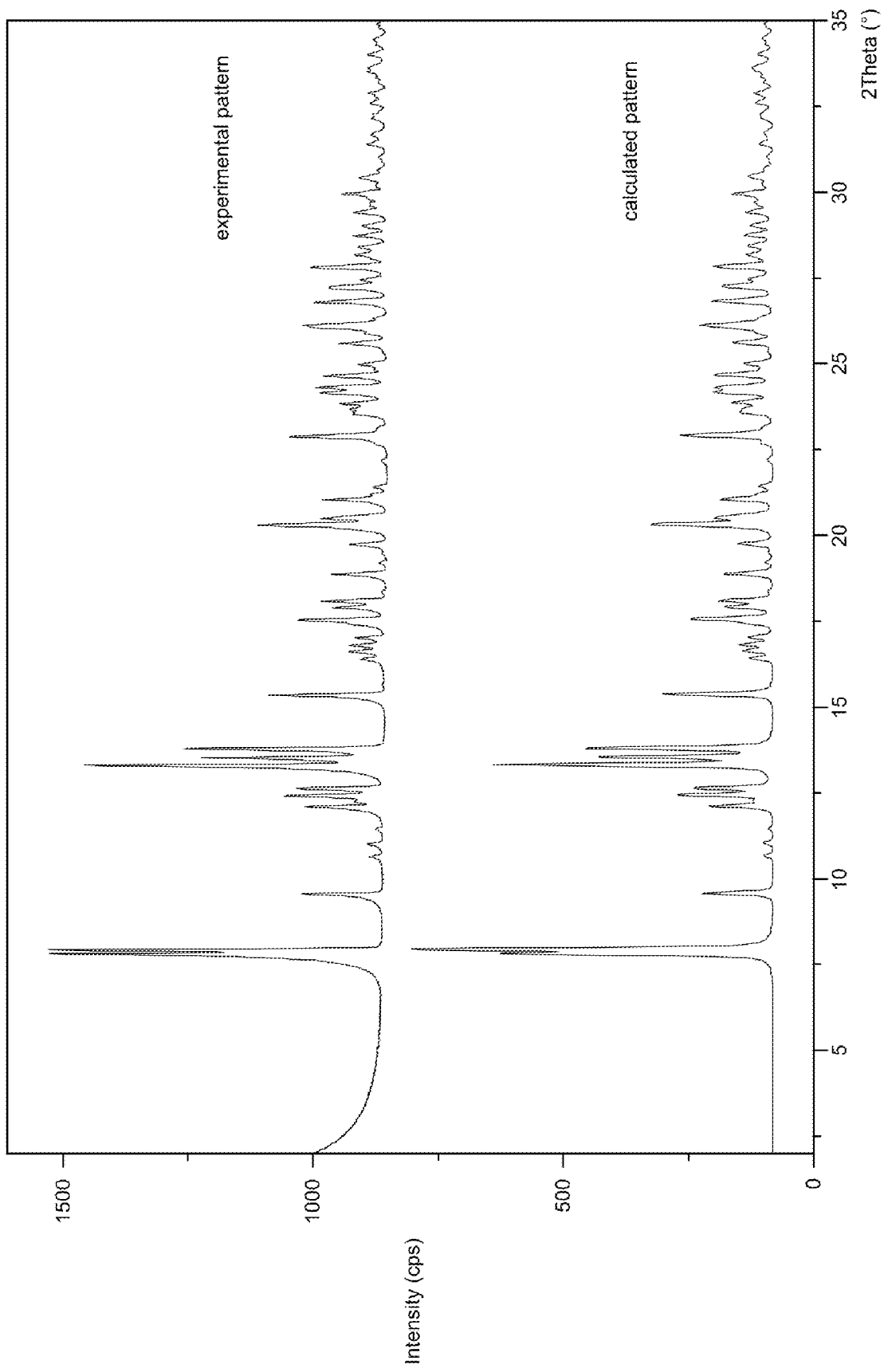
FIG. 14: Experimental and calculated X-ray powder diffractograms of (S)-(−)-blarcamesine hydrobromide, (R)-(+)-blarcamesine hydrobromide, ZnBr$_2$ (1:1:1) co-crystal (2d)

With single crystal X-ray diffraction the exact atomic positions can be determined in the crystal. Based on these data, the powder X-ray diffraction pattern can be calculated. Experimental and calculated powder X-ray diffraction patterns of (S)-(−)-blarcamesine hydrobromide, (R)-(+)-blarcamesine hydrobromide, ZnBr$_2$ (1:1:1) co-crystal (2d) are identical (FIG. 14.), therefore the presented crystal phase is pure and uniform.

| Measurement conditions | |
|---|---|
| Single-crystal X-ray diffraction parameters | |
| Instrument: | Rigaku R-AXIS SPIDER diffractometer |
| Detection: | Image plate |
| X-ray tube | |
| Type: | Rigaku Long Fine Focus |
| Anode: | Cu |
| Wawelength: | Kα (1,541874 Å) |
| X-ray powder diffraction instrument settings | |
| Instrument: | PANalytical Empyrean X-ray powder diffractometer |
| Sample mode: | Transmission |
| X-ray tube | |
| Type: | Empyrean Long Fine Focus High Resolution tube |
| Anode material: | Cu |
| Wavelength: | Kα (1.541874 Å) |
| Focus mode: | line focus |
| Incident beam optics | |
| Divergence slit: | Fixed slit 1/2° |
| Mirror: | Focusing elliptical mirror |
| Soller slit: | 0.04 rad |
| Anti-scatter slit: | Fixed slit 1/2° |
| Diffracted beam optics | |
| Anti-scatter slit: | Programmable slit in fix mode: 1/2° |
| Soller slit: | 0.04 rad |
| Sample stage | |
| Type: | Reflection-transmission spinner stage |
| Sample rotation: | 1 rps |
| Beam knife: | Transmission beam stop used |
| Detector | |
| Type: | PIXcel 3D 1 × 1 area detector |
| Mode: | Scanning line detector (1D) mode |
| Active length: | 3.3473° |
| Sample preparation: | place powder samples (without grinding) between two Mylar foils in the sample holder |

| Measurement conditions | |
|---|---|
| Measurement settings | |
| Temperature: | room temperature |
| Accelerating voltage: | 45 kV |
| Anode current: | 40 mA |
| Scan type: | continuous gonio (θ/θ) scan |
| Measurement range: | range: 2.0000 – 34.9964 °2θ |
| Step size: | 0.0131 °2θ |
| Time per step: | 109.650 s |
| Measurement cycles: | 1 |
| Measurement time: | ~20 minutes |
| Thermogravimetry instrument settings | |
| Device: | TA Instruments Discovery TGA thermogravimetric analyzer |
| Atmosphere: | N$_2$ flow: 25 mL/min (furnace) 10 mL/min (balance) |
| Data sampling interval: | 0,5 s/pt |
| Temperature program (2a): | 30° C.-240° C.   10° C./min |
| Temperature program (2b, 2c): | 30° C.-200° C.   10° C./min |
| Pan: | Platinum 100 μL |
| Differential scanning calorimetry instrument settings | |
| Device: | TA Instruments Discovery DSC differential scanning calorimeter |
| Atmosphere: | N$_2$ flow (50 mL/min) |
| Data sampling interval: | 0,1 s/pt |
| Temperature program (2a): | 35° C.-250° C.   10° C./min |
| Temperature program (2b, 2c): | 30° C.-190° C.   10° C./min |
| Pan (2a) | Hermetically sealed Al |
| Pan (2b, 2c) | Standard Al sealed |

EXAMPLES

The following examples are included for the purpose of illustration of the disclosure and are to be construed by way of example and not as a limitation.

Example 1

Preparation of (S)-(−)-blarcamesine hydrochloride, (R)-(+)-blarcamesine hydrochloride, ZnCl$_2$ (1:1:1) co-crystal (2a)

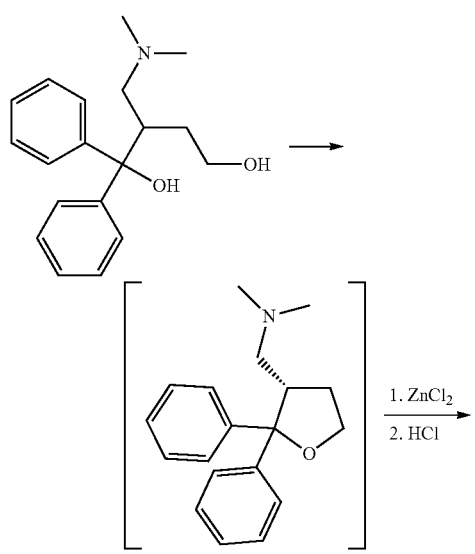

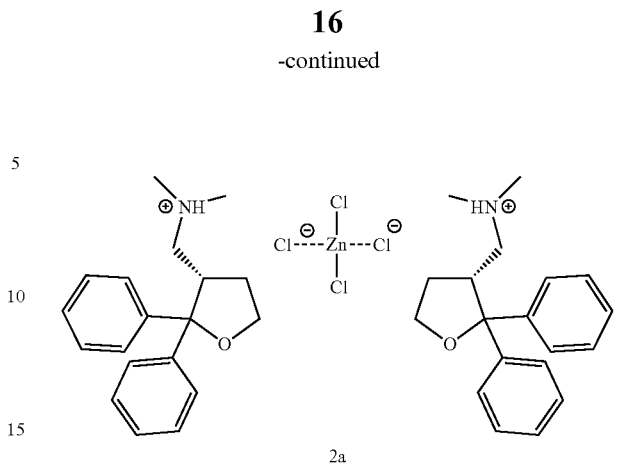

2a

To a round bottom flask filled with toluene solution of 2-[(dimethylamino)methyl]-1,1-diphenylbutane-1,4-diol (3.68 g, 12.29 mmol) p-toluenesulfonic acid was added. The mixture was refluxed with Dean-Stark apparatus for water removal. After the completion of the reaction the toluene solution were washed with aq. NaOH solution then brine, and dried. Isopropyl alcohol (IPA) (12 mL) was added to the residual 40 mL solution and warmed to 80° C. While continuous stirring, at first a pre-prepared 80° C. toluene-IPA (1:1) ZnCl$_2$ solution (0.92 g, 6.76 mmol, 0.55 mol eq., dissolved in 6 mL solvent) then a 6.25 M IPA/HCl solution (2.16 mL, 13.52 mmol, 1.1 mol eq.) was added. The mixture was stirred further, and the precipitated solid was filtered off still in warm. The solid crystalline material was washed and dried in vacuum until constant weight, obtaining 4.34 g (91.5%) white (S)-(−)-blarcamesine hydrochloride, (R)-(+)-blarcamesine hydrochloride, ZnCl$_2$ (1:1:1) co-crystal.

HPLC purity: 99.5%.

HPLC purity: 99.97% (after crystallization from aq. IPA)

Mp.: 234-236° C.

Zn content (complexometric titration): 8.67% (calculated: 8.47%)

$^1$H-NMR (DMSO, 600 MHz): 9.94 (bs, 1H); 7.63 (~d, J=8.4 Hz, 2H); 7.42 (~d, J=8.3 Hz, 2H); 7.35 (m, 2H); 7.31 (m, 2H); 7.24 (~t, J=7.3 Hz, 1H); 7.20 (~t, J=7.3 Hz, 1H); 4.17 (q, J=7.8 Hz 1H); 3.76 (td, J=8.8, 4.7 Hz, 1H); 3.59 (m, 1H); 2.83 (bs, 3H); 2.73 (bs, 3H); 2.72 (m, 2H); 2.25 (m, 1H); 1.92 (m, 1H). $^{13}$C-NMR (DMSO, 150 MHz): 145.51; 142.64; 128.62; 128.50; 127.24; 127.01; 126.01; 125.57; 89.32; 64.58; 57.89; 44.86; 41.33; 40.99; 28.52.

COSY: 9.94-2.83; 2.73; 7.63-7.35-7.24; 7.42-7.31-7.20; (4.17; 3.76)-(2.25; 1.92)-3.59; 2.73.

HSQC: 7.63-125.57; 7.42-126.01; 7.35-128.62; 7.31-128.50; 7.24-127.24; 7.20-127.01; (4.17; 3.76)-64.58; 3.59-40.99; 2.83-41.33; 2.73-44.86; 2.72-57.89; (2.25; 1.92)-28.52.

HMBC (characteristic cross peaks): 7.63-89.32; 7.42-89.32; 7.35-145.51; 7.31-142.64; 4.17-89.32.

Elemental analysis C$_{38}$H$_{48}$Cl$_4$N$_2$O$_2$Zn (M: 771.99) calculated: C 59.12%; H 6.27%; N 3.63%; Cl 18.37% measured: C 59.17%; H 6.39%; N 3.57%; Cl 18.46%

Example 2

(S)-(−)-blarcamesine hydrochloride, ZnCl₂ (2:1) co-crystal (2b)

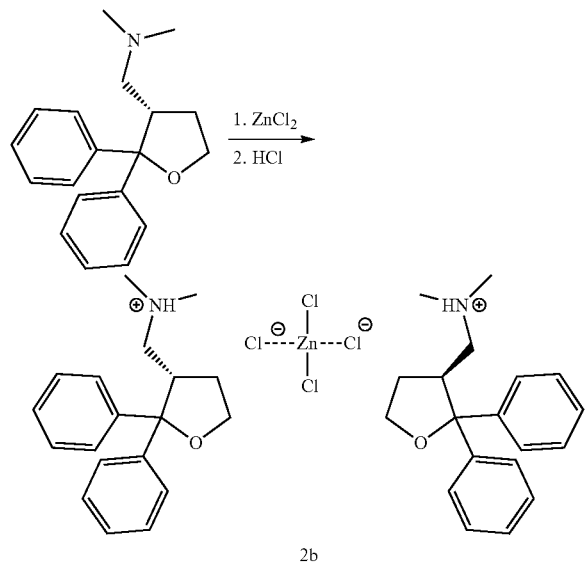

2b (S)-(−)-blarcamesine base (1.50 g, 5.33 mmol) was dissolved in IPA (10 mL), then warmed to 80° C. A pre-prepared 80° C. IPA solution of ZnCl₂ (0.40 g, 2.93 mmol, dissolved in 5 mL solvent) then a 6.25 M IPA/HCl solution (0.94 mL, 5.86 mmol, 1.1 mol eq.) was added. The mixture was stirred further, and the precipitated solid was filtered off still in warm. The solid crystalline material was dried in vacuum until constant weight, yielding 1.80 g (87.5%) white (S)-(−)-blarcamesine hydrochloride, ZnCl₂ (2:1) co-crystal.

HPLC purity: 99.9%

Mp.: 176-178° C.

Zn content (complexometric titration): 8.76% (calculated: 8.47%)

$^1$H-NMR (DMSO, 600 MHz): 9.90 (b, 1H); 7.62 m, 2H); 7.41 m, 2H); 7.35 (m, 2H); 7.31 (m, 2H); 7.24 (m, 1H); 7.20 (m, 1H); 4.17 (m, 1H); 3.76 (m, 1H); 3.58 (m, 1H); 2.75 (b, 3H); 2.75 (b, 3H); 2.70 (b, 2H); 2.24 (m, 1H); 1.92 (m, 1H).

$^{13}$C-NMR (DMSO, 150 MHz): 145.53; 142.66; 128.63; 128.50; 127.25; 127.01; 126.02; 125.58; 89.31; 64.59; 57.95; 44.85.

COSY: 7.62-7.35-7.24; 7.41-7.31-7.20; (4.17; 3.76)-(2.24; 1.92)-3.58; 2.70.

HSQC (140 Hz): 7.62-125.58; 7.41-126.02; 7.5-128.63; 7.31-128.50; 7.24-127.25; 7.20-127.01; 4.17-64.59; 3.76-64.59; 3.58-41.04; 2.75-41.37; 2.75-44.85; 2.70-57.95; 2.24-28.52; 12.92-28.52.

HMBC (8 Hz, 140 Hz): 7.62-(127.25; 125.58; 89.31); 7.41-(127.01; 126.02; 89.31); 7.35-(145.53; 128.63); 7.31-(124.66; 128.5); 7.24-125.58; 7.20-126.02; (4.17; 3.76)-(89.31; 41.04; 28.52); 3.58-(64.59; 57.95); (2.24; 1.92)-(89.31; 64.59; 41.04).

Elemental analysis $C_{38}H_{48}Cl_4N_2O_2Zn$ (M: 771.99) calculated: C 59.12%; H 6.27%; N 3.63%; Cl 18.37% measured: C 58.73%; H 6.40%; N 3.57%; Cl 18.82%

Example 3

(R)-(+)-blarcamesine hydrochloride, ZnCl₂ (2:1) co-crystal (2c)

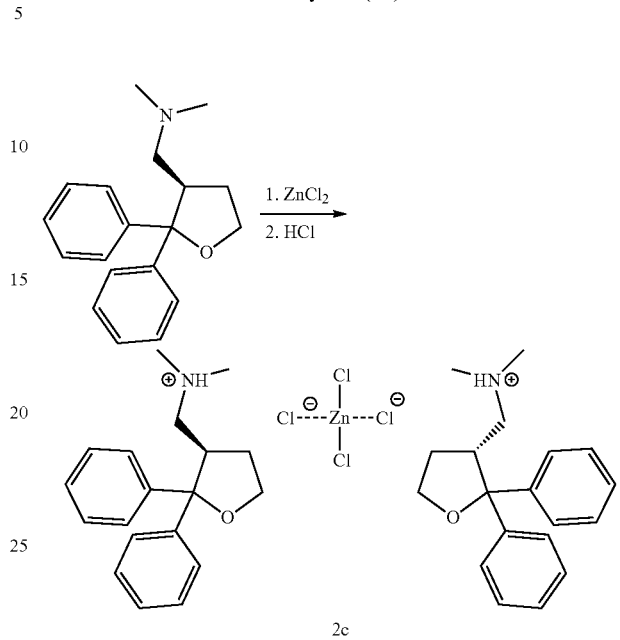

2c (R)-(+)-blarcamesine base (1.50 g, 5.33 mmol) was dissolved in IPA (10 mL), then warmed to 80° C. A pre-prepared 80° C. IPA solution of ZnCl₂ (0.40 g, 2.93 mmol, dissolved in 5 mL solvent) then a 6.25 M IPA/HCl solution (0.94 mL, 5.86 mmol, 1.1 mol eq.) was added. The mixture was stirred further, and the precipitated solid was filtered off still in warm. The solid crystalline material was dried in vacuum until constant weight, yielding 1.94 g (94.3%) white (R)-(+)-blarcamesine hydrochloride, ZnCl₂ (2:1) co-crystal.

HPLC purity: 99.73%

Mp.: 176-178° C.

Zn content (complexometric titration): 8.79% (calculated: 8.47%)

$^1$H-NMR (DMSO, 600 MHz): 9.93 (b, 1H, 7.62 (m, 2H); 7.42 (m, 2H); 7.35 (m, 2H); 7.31 (m, 2H); 7.24 (m, 1H); 7.20 (m, 1H); 4.18 (m, 1H); 3.77 (m, 1H); 3.59 (m, 1H); 2.83 (b, 3H); 2.74 (b, 3H); 2.72 (b, 2H); 2.26 (m, 1H); 1.93 (m, 1H).

$^{13}$C-NMR (DMSO, 150 MHz): 145.50; 142.64; 128.63; 128.50; 127.25; 127.02; 126.01; 125.57; 89.33; 64.59; 57.90; 44.87.

COSY: 7.62-7.35-7.24; 7.42-7.31-7.20; (4.18; 3.77)-(2.26; 1.92)-3.59-2.72.

ROESY: 4.18-2.26; 3.59-(7.62; 1.92).

HSQC (140 Hz): 7.62-125.57; 7.42-126.01; 7.35-128.63; 7.31-128.50; 7.24-127.25; 7.20-127.02; 4.18-64.59; 3.77-64.59; 3.59-41.00; 2.83-41.34; 2.74-44.87; 2.72-57.90; 2.26-28.53; 1.93-28.53.

HMBC (8 Hz, 140 Hz): 7.62-(127.25; 125.57; 89.33); 7.42-(127.02; 126.01; 89.33); 7.35-(145.50; 128.63); 7.31-(142.64; 128.50); 7.24-125.57; 7.20-126.01; (4.18; 3.77)-(89.33; 41.00; 28.53); 3.59-(64.59; 57.90); 2.72-(41.00; 28.53); (2.26; 1.93)-(89.33; 64.59; 57.90; 41.00).

Elemental analysis $C_{38}H_{48}Cl_4N_2O_2Zn$ (M: 771.99) calculated: C 59.12%; H 6.27%; N 3.63%; Cl 18.37% measured: C 58.96%; H 6.40%; N 3.61%; Cl 18.39%

Example 4

(S)-(−)-blarcamesine hydrobromide, (R)-(+)-blarcamesine hydrobromide, ZnBr$_2$ (1:1:1) co-crystal (2d)

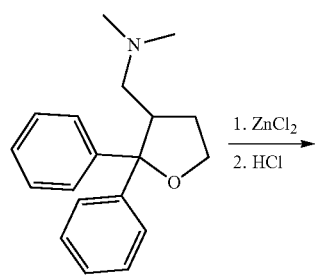

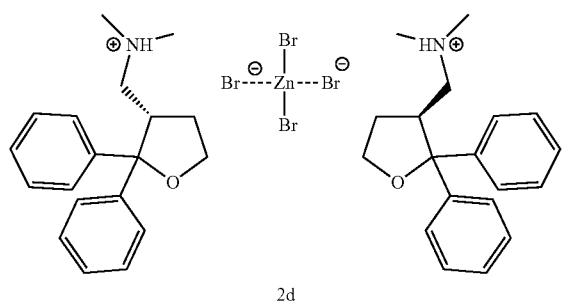

2d

Using the method described in examples 2 and 3, 0.53 g of (S)-(−)-blarcamesine hydrobromide, (R)-(+)-blarcamesine hydrobromide, ZnBr$_2$ (1:1:1) co-crystal was prepared.

Mp.: 181-183,5° C.

$^1$H-NMR (DMSO, 600 MHz): 7.59 (m, 2H); 7.36 (m, 2H); 7.34 (m, 2H); 7.28 (m, 2H); 7.23 (m, 1H); 7.17 (m, 1H); 4.11 (m, 1H); 3.72 (m, 1H); 3.38 (b, 1H); 2.46 (b, 6H); 2.30 (b, 2H); 2.09 (m, 1H); 1.86 (m, 1H). $^{13}$C-NMR (DMSO, 150 MHz): 146.06; 143.19; 128.54; 128.22; 127.10; 126.75; 126.13; 125.75; 89.16; 64.68; 59.20; 44.69; 42.32; 28.59.

COSY: 7.59-7.34-7.23; 7.36-7.28-7.17; (4.11; 3.72)-(2.09; 1.86)-3.38.

HSQC (140 Hz): 7.59-125.75; 7.36-126.13; 7.34-128.54; 7.28-128.22; 7.23-127.10; 7.17-126.75; 4.11-64.68; 7.32-64.68; 3.38-42.32; 2.46-44.69; 2.30-59.20; 2.09-28.59; 1.86-28.59.

HMBC (8 Hz, 140 Hz): 7.59-(127.10; 125.75; 89.16); 7.36-(126.75; 126.13; 89.16); 7.34-(146.06; 128.54); 7.28-(143.19; 128.22); 7.23-125.75; 7.17-126.13; (4.11; 3.72)-(89.16; 42.32; 28.59); (2.09; 1.86)-(89.16; 64.65; 59.20; 42.32).

Elemental analysis C$_{38}$H$_{48}$Br$_4$N$_2$O$_2$Zn (M: 949.81) calculated: C 48.05%; H 5.09%; N 2.95%; Br 33.65% measured: C 45.52%; H 4.71%; N 2.79%; Br 32.52%

The invention claimed is:

1. A co-crystal selected from the group consisting of a racemic co-crystal of formula 2a consisting of one molecule of (R) and one molecule of (S) configuration of blarcamesine hydrochloride and one molecule of ZnCl$_2$ per unit cell

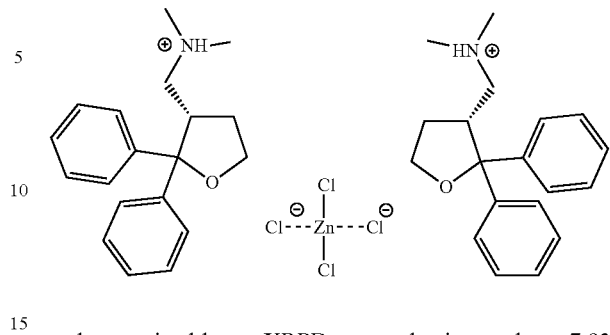

characterized by an XRPD pattern having peaks at 7.93; 9.66; 13.73; 15.77; 16.73; and 17.82° 2θ±0.2° 2θ;

a co-crystal of formula 2b consisting of two molecules of (S) configuration of blarcamesine hydrochloride and one molecule of ZnCl$_2$ per unit cell

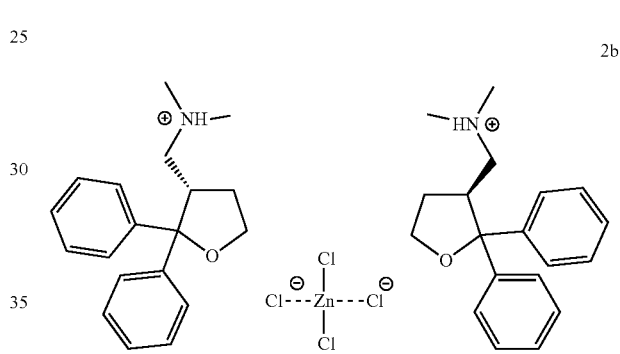

characterized by an XRPD pattern having peaks at 12.15; 12.85; 13.04; 13.24; 16.36; and 19.67° 2θ±0.2° 2θ; and a co-crystal of formula 2c consisting of two molecules of (R) configuration of blarcamesine hydrochloride and one molecule of ZnCl$_2$ per unit cell

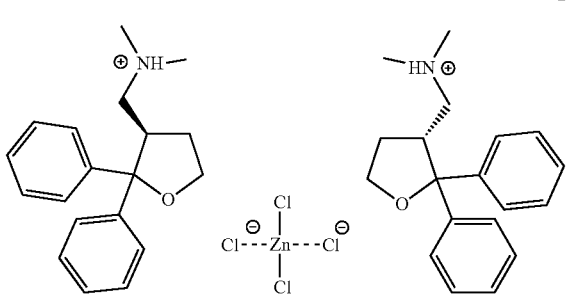

characterized by an XRPD pattern having peaks at 12.15; 12.85; 13.04; 13.24; 16.36; and 19.67° 2θ±0.2° 2θ.

2. The co-crystal according to claim 1 wherein the co-crystal is the racemic co-crystal of formula 2a consisting of one molecule of (R) and one molecule of (S) configuration of blarcamesine hydrochloride and one molecule of ZnCl$_2$ per unit cell 2a

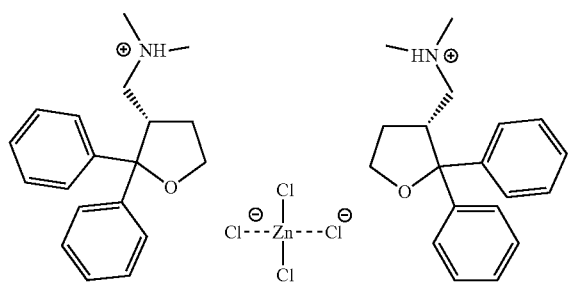

characterized by an XRPD pattern having peaks at 7.93; 9.66; 13.73; 15.77; 16.73; and 17.82° 2θ±0.2° 2θ.

3. The co-crystal according to claim 2 characterized by the following data:
the N(+)-Cl(−) distance is 0.31-0.33 nm.

4. The co-crystal according to claim 1 wherein the co-crystal is the co-crystal of formula 2b consisting of two molecules of (S) configuration of blarcamesine hydrochloride and one molecule of ZnCl$_2$ per unit cell 2b

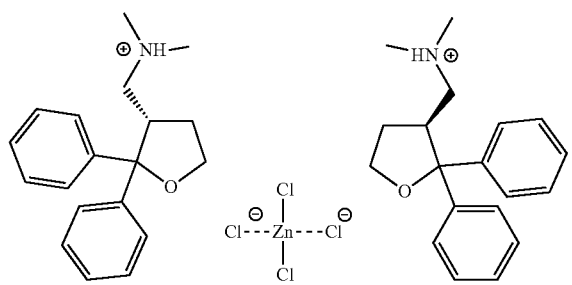

characterized by an XRPD pattern having peaks at 12.15; 12.85; 13.04; 13.24; 16.36; and 19.67° 2θ±0.2° 2θ.

5. The co-crystal according to claim 4 characterized by the following data:
the N(+)-Cl(−) distance is 0.31-0.33 nm.

6. The co-crystal according to claim 1 wherein the co-crystal is the co-crystal of formula 2c consisting of two molecules of (R) configuration of blarcamesine hydrochloride and one molecule of ZnCl$_2$ per unit cell 2c

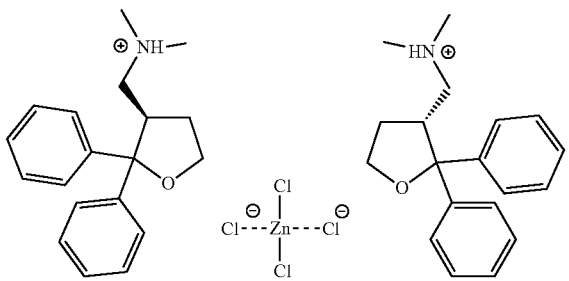

characterized by an XRPD pattern having peaks at 12.15; 12.85; 13.04; 13.24; 16.36; and 19.67° 2θ±0.2° 2θ.

7. The co-crystal according to claim 6 characterized by the following data:
the N(+)-Cl(−) distance is 0.31-0.33 nm.

8. A pharmaceutical dosage form comprising a therapeutically effective amount of the co-crystal of formula 2a according to claim 1 and at least one therapeutically acceptable excipient.

9. A pharmaceutical dosage form comprising a therapeutically effective amount of the co-crystal of formula 2b according to claim 1 and at least one therapeutically acceptable excipient.

10. A pharmaceutical dosage form comprising a therapeutically effective amount of the co-crystal of formula 2c according to claim 1 and at least one therapeutically acceptable excipient.

* * * * *